United States Patent
Cassayre

(10) Patent No.: US 6,933,260 B2
(45) Date of Patent: Aug. 23, 2005

(54) AVERMECTIN B1 DERIVATIVES HAVING AN AMINOSULFONYLOXY SUBSTITUENT IN THE 4'-POSITION

(75) Inventor: Jérôme Cassayre, Basel (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 10/498,858

(22) PCT Filed: Dec. 20, 2002

(86) PCT No.: PCT/EP02/14671

§ 371 (c)(1),
(2), (4) Date: Jun. 14, 2004

(87) PCT Pub. No.: WO03/053988

PCT Pub. Date: Jul. 3, 2003

(65) Prior Publication Data

US 2005/0032717 A1 Feb. 10, 2005

(30) Foreign Application Priority Data

Dec. 21, 2001 (CH) .............................................. 2363/01
Jul. 5, 2002 (CH) .............................................. 1190/02

(51) Int. Cl.[7] ........................ A01N 25/26; A01N 43/02; A01N 57/18; A61K 31/33; C07D 313/00
(52) U.S. Cl. ........................ 504/100; 504/140; 504/208; 514/183; 549/354
(58) Field of Search ................................ 504/100, 140, 504/208; 514/183; 549/354

(56) References Cited

U.S. PATENT DOCUMENTS 4,427,663 A    1/1984   Mrozik

OTHER PUBLICATIONS

Mrozik H et al.: "4–deoxy–r–aminoavermectins with potent broad spectrum antiparasitic activities" Bioorganic & Medicinal Chemistry Letters, Oxford, GB, vol. 5, No. 20, (Oct. 19, 1995), pp. 2435–2440, ISSN: 0960–894X.

*Primary Examiner*—Alton Pryor
(74) *Attorney, Agent, or Firm*—Rose M. Allen

(57) ABSTRACT

A compound of formula (I) wherein the bond marked by formula (II) indicates either the S or the R isomer at the 4"-position; and wherein $R_1$ is $C_1-C_{12}$alkyl, $C_3-C_8$cycloalkyl; or $C_2-C_{12}$alkenyl; $R_2$ is, for example, hydrogen, unsubstituted or mono- to penta-substituted $C_1-C_{12}$alkyl or unsubstituted or mono- to penta-substituted $C_2-C_{12}$alkenyl; $R_3$ is, for example, hydrogen, $C_1-C_{12}$alkyl, mono- to penta-substituted $C_1-C_{12}$alkyl, unsubstituted or mono- to penta-substituted $C_3-C_{12}$cycloalkyl, or unsubstituted or mono- to penta-substituted $C_2-C_{12}$alkenyl; and wherein the substituents of the alkyl, alkenyl, alkynyl, alkylene, alkenylene and cycloalkyl radicals defined under $R_2$ and $R_3$ are selected, for example, from the group consisting of OH, halogen, halo-$C_1-C_2$alkyl, CN, $NO_2$ and $C_2-C_6$alkynyl; and, where applicable, E/Z isomers, mixtures of E/Z isomers and/or tautomers, in each case in free form or in salt form; a process for the preparation of and the use of those compounds, their isomers and tautomers; starting materials for the preparation of the compounds of formula (I); pesticidal compositions in which the active ingredient has been selected from those compounds and their tautomers; and a method of controlling pests using those compositions are described.

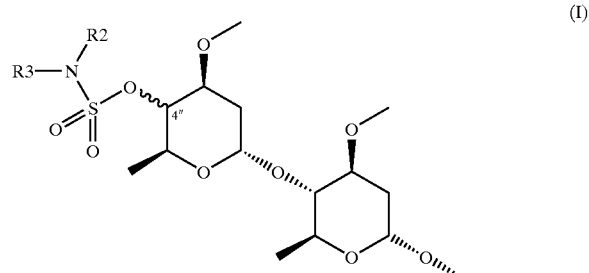

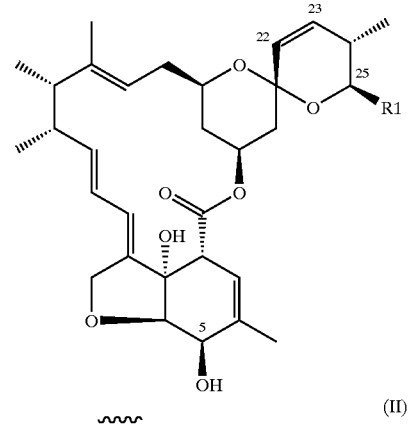

6 Claims, No Drawings

AVERMECTIN B1 DERIVATIVES HAVING AN AMINOSULFONYLOXY SUBSTITUENT IN THE 4'-POSITION

This application is a 371 of International Application No. PCT/EP02/14671 filed Dec. 20, 2002, which claims priority to CH 2363/01, filed Dec. 21, 2001, and CH1190/02, filed Jul. 5, 2002, the contents of which are incorporated herein by reference.

The invention relates to (1) a compound of formula

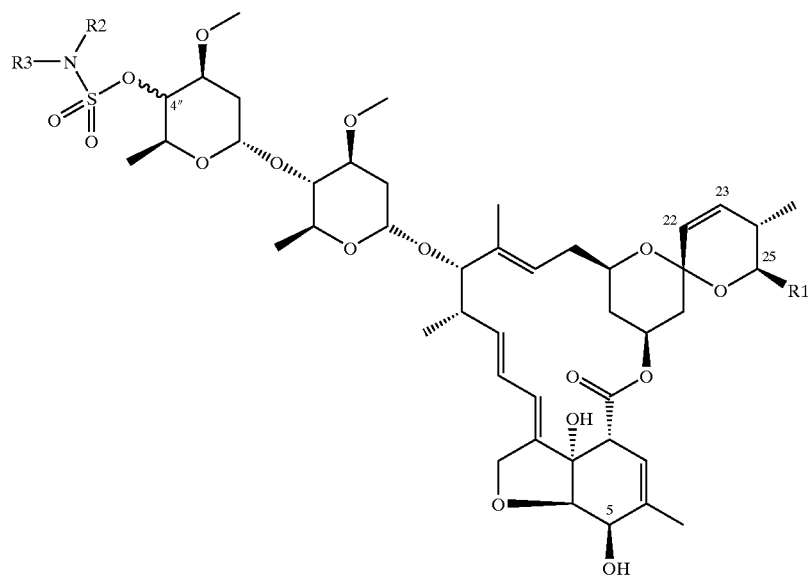

(I)

wherein $R_1$ is $C_1$–$C_{12}$alkyl, $C_3$–$C_8$cycloalkyl; or $C_2$–$C_{12}$alkenyl;

$R_2$ is hydrogen, unsubstituted or mono- to penta-substituted $C_1$–$C_{12}$alkyl or unsubstituted or mono- to penta-substituted $C_2$–$C_{12}$alkenyl; unsubstituted or mono- to penta-substituted $C_2$–$C_{12}$alkynyl; —C(O)$R_4$ or SO$_2R_4$;

$R_3$ is hydrogen, $C_1$–$C_{12}$alkyl, mono- to penta-substituted $C_1$–$C_{12}$alkyl, unsubstituted or mono- to penta-substituted $C_3$–$C_{12}$cycloalkyl, unsubstituted or mono- to penta-substituted $C_2$–$C_{12}$alkenyl; or unsubstituted or mono- to penta-substituted $C_2$–$C_{12}$alkynyl; or $R_2$ and $R_3$ together are a three- to seven-membered alkylene bridge or a four- to seven-membered alkenylene bridge wherein one CH$_2$ group in the alkylene or alkenylene may have been replaced by O, S or NR$_5$; or are a group =N$^+$=N$^-$, and wherein the substituents of the alkyl, alkenyl, alkynyl, alkylene, alkenylene and cycloalkyl radicals defined under $R_2$ and $R_3$ are selected from the group consisting of OH, halogen, halo-$C_1$–$C_2$alkyl, CN, NO$_2$, $C_2$–$C_6$alkynyl; $C_3$–$C_8$cycloalkyl unsubstituted or substituted by from one to three methyl groups, norbornylenyl; $C_3$–$C_8$cycloalkenyl unsubstituted or substituted by from one to three methyl groups; $C_3$–$C_8$halocycloalkyl, $C_1$–$C_{12}$alkoxy, $C_1$–$C_6$-alkoxy-$C_1$–$C_6$alkyl, $C_1$–$C_6$alkoxy-$C_1$–$C_6$alkoxy-$C_1$–$C_6$alkyl, $C_3$–$C_8$cycloalkoxy, $C_1$–$C_{12}$haloalkoxy, $C_1$–$C_{12}$alkylthio, $C_3$–$C_8$cycloalkylthio, $C_1$–$C_{12}$haloalkylthio, $C_1$–$C_{12}$alkylsulfinyl, $C_3$–$C_8$cycloalkyl-sulfinyl, $C_1$–$C_{12}$haloalkylsulfinyl, $C_3$–$C_8$halocycloalkylsulfinyl, $C_1$–$C_{12}$alkylsulfonyl, $C_3$–$C_8$cycloalkylsulfonyl, $C_1$–$C_{12}$haloalkylsulfonyl, $C_3$–$C_8$halocycloalkylsulfonyl, $C_2$–$C_8$alkenyl, $C_2$–$C_8$alkynyl, NH($C_1$–$C_6$alkyl), N($C_1$–$C_6$alkyl)$_2$, —C(=O)$R_4$, —NHC(=O)$R_7$, —P(=O)(O$C_1$–$C_6$alkyl)$_2$; aryl, heterocyclyl, aryloxy, heterocyclyloxy; and aryl, heterocyclyl, aryloxy and heterocyclyloxy that, depending upon the possibilities of substitution at the ring, are mono- to penta-substituted by substituents selected from the group consisting of OH, halogen, CN, NO$_2$, $C_1$–$C_{12}$alkyl, $C_3$–$C_8$cycloalkyl, $C_1$–$C_{12}$haloalkyl, $C_1$–$C_{12}$alkoxy, $C_1$–$C_{12}$haloalkoxy, $C_1$–$C_{12}$alkylthio, $C_1$–$C_{12}$haloalkylthio, $C_1$–$C_6$alkoxy-$C_1$–$C_6$alkyl, dimethylamino-$C_1$–$C_6$alkoxy, $C_2$–$C_8$alkenyl, $C_2$–$C_8$-alkynyl, phenoxy, phenyl-$C_1$–$C_6$alkyl; phenoxy unsubstituted or substituted by from one to three substituents selected independently of one another from halogen, methoxy, trifluoromethyl and trifluoromethoxy; phenyl-$C_1$–$C_6$alkoxy unsubstituted or substituted in the aromatic ring by from one to three substituents selected independently of one another from halogen, methoxy, trifluoromethyl and trifluoromethoxy; phenyl-$C_2$–$C_6$alkenyl, phenyl-$C_2$–$C_6$alkynyl, methylenedioxy, —C(=O)$R_4$, —O—C(=O)$R_7$, —NH—C(=O)$R_7$, NH$_2$, NH($C_1$–$C_{12}$alkyl), N($C_1$–$C_{12}$alkyl)$_2$, $C_1$–$C_6$alkylsulfinyl, $C_3$–$C_8$cycloalkylsulfinyl, $C_1$–$C_6$haloalkylsulfinyl, $C_3$–$C_8$halocycloalkylsulfinyl, $C_1$–$C_6$alkylsulfonyl, $C_3$–$C_8$cycloalkylsulfonyl, $C_1$–$C_6$haloalkylsulfonyl and $C_3$–$C_8$halocycloalkylsulfonyl;

$R_4$ is H, OH, $C_1$–$C_8$alkyl, $C_1$–$C_8$alkyl mono- to hepta-substituted by halogen, nitro, $C_1$–$C_8$alkoxy, OH, SH, NH$_2$, NH($C_1$–$C_{12}$alkyl) or N($C_1$–$C_{12}$alkyl)$_2$; $C_1$–$C_8$alkoxy, halo-$C_1$–$C_8$-alkoxy, $C_3$–$C_8$cycloalkyl, $C_3$–$C_8$cycloalkoxy, $C_2$–$C_8$alkenyl, $C_2$–$C_8$alkenyloxy, $C_2$–$C_8$alkynyl, $C_2$–$C_8$alkynyloxy, NH$_2$, NH($C_1$–$C_{12}$alkyl), N($C_1$–$C_{12}$alkyl)$_2$, aryl, aryloxy, benzyl, benzyloxy, heterocyclyl, heterocyclyloxy, heterocyclylmethyl or heterocyclylmethoxy; wherein the radicals aryl, aryloxy, benzyl, benzyloxy, heterocyclyl, heterocyclyloxy, heterocyclylmethyl and heterocyclylmethoxy are unsubstituted or, depending upon the possibilities of substitution at the ring, are substituted by from one to three substituents selected independently of one another from halogen, $C_1$–$C_{12}$alkyl, $C_1$–$C_{12}$haloalkyl, $C_1$–$C_{12}$alkoxy, $C_1$–$C_{12}$haloalkoxy, $C_1$–$C_6$alkoxy-$C_1$–$C_6$alkoxy, $C_1$–$C_{12}$alkylthio, $C_1$–$C_{12}$haloalkylthio, $C_2$–$C_8$alkenyloxy, $C_2$–$C_8$alkynyloxy, nitro and cyano;

$R_5$ is $C_1$–$C_8$alkyl, $C_3$–$C_8$cycloalkyl, $C_2$–$C_8$alkenyl, $C_2$–$C_8$alkynyl, benzyl or —C(=O)—$R_6$;

$R_6$ is H, OH, SH, $NH_2$, NH($C_1$–$C_{12}$alkyl), N($C_1$–$C_{12}$alkyl)$_2$, $C_1$–$C_{12}$alkyl, $C_1$–$C_{12}$haloalkyl, $C_1$–$C_{12}$alkoxy, $C_1$–$C_{12}$haloalkoxy, $C_1$–$C_6$alkoxy-$C_1$–$C_6$alkoxy, $C_1$–$C_{12}$alkylthio, $C_2$–$C_8$alkenyloxy, $C_2$–$C_8$alkynyloxy; phenyl, phenoxy, benzyloxy, NH-phenyl, N($C_1$–$C_6$alkyl)-phenyl, NH—$C_1$–$C_6$-alkyl-C(=O)—$R_6$, N($C_1$–$C_6$alkyl)-$C_1$–$C_6$alkyl-C(=O)—$R_8$; or phenyl, phenoxy, benzyloxy, NH-phenyl or N($C_1$–$C_6$alkyl)-phenyl each of which is substituted in the aromatic ring by from one to three substituents selected independently of one another from halogen, $C_1$–$C_6$alkoxy, $C_1$–$C_6$haloalkyl and $C_1$–$C_6$haloalkoxy;

$R_7$ is H, $C_1$–$C_{12}$alkyl, $C_1$–$C_{12}$haloalkyl, $C_2$–$C_8$alkenyl, $C_2$–$C_8$alkynyl, phenyl, benzyl, $NH_2$, NH($C_1$–$C_{12}$alkyl), N($C_1$–$C_{12}$alkyl)$_2$, NH-phenyl or N($C_1$–$C_{12}$alkyl)-phenyl; and $R_8$ is H, OH, $C_1$–$C_{12}$alkyl, $C_1$–$C_{12}$alkoxy, $C_1$–$C_6$alkoxy-$C_1$–$C_6$alkoxy, $C_2$–$C_8$alkenyloxy, phenyl, phenoxy, benzyloxy, $NH_2$, NH($C_1$–$C_{12}$alkyl), N($C_1$–$C_{12}$alkyl)$_2$, NH-phenyl or N($C_1$–$C_{12}$-alkyl)-phenyl;

and, where applicable, to E/Z isomers, mixtures of E/Z isomers and/or tautomers, in each case in free form or in salt form;

to a process for the preparation of and to the use of those compounds and their isomers and tautomers; to starting materials for the preparation of the compounds of formula (I); to pesticidal compositions in which the active ingredient has been selected from the compounds of formula (I) and their tautomers; and to a method of controlling pests using those compositions.

Hereinbefore and hereinafter, the bond marked by the symbol $\sim$ in formulae (I), (II) and (IV) indicates that at the 4"-position the S- as well as the R-isomer is meant.

Certain macrolide compounds are proposed for pest control in the literature. The biological properties of those known compounds are not entirely satisfactory, however, for which reason there is a need to provide further compounds having pesticidal properties, especially for the control of insects and members of the order Acarina. That problem is solved according to the invention by the provision of the present compounds of formula (I).

The compounds claimed according to the invention are derivatives of avermectin. Avermectins are known to the person skilled in the art. They are a group of structurally closely related pesticidally active compounds which are obtained by fermentation of a strain of the microorganism *Streptomyces avermitilis*. Derivatives of avermectins can be obtained via conventional chemical syntheses.

The avermectins obtainable from *Streptomyces avermitilis* are designated A1a, A1b, A2a, A2b, B1a, B1b, B2a and B2b. Compounds with the designation "A" have a methoxy radical in the 5-position; those compounds designated "B" have an OH group. The "a" series comprises compounds wherein the substituent $R_1$ (in position 25) is a sec-butyl radical; in the "b" series there is an isopropyl radical in the 25-position. The number 1 in the name of a compound indicates that atoms 22 and 23 are bonded by a double bond; the number 2 indicates that they are bonded by a single bond and carbon atom 23 carries an OH group. The above designations are retained in the description of the present invention in order in the case of the non-natural avermectin derivatives according to the invention to indicate the specific structural type corresponding to natural avermectin. There are claimed according to the invention derivatives of compounds of the B1 series, more especially mixtures of derivatives of avermectin B1a and B1b having, at the 4"-position, either the S- or the R-configuration.

Some of the compounds of formula (I) may be in the form of tautomers. Accordingly, any reference to the compounds of formula (I) hereinbefore and hereinafter is to be understood, where applicable, as including also corresponding tautomers, even if the latter are not specifically mentioned in every case.

The compounds of formula (I) and, where applicable, their tautomers can form salts, for example acid addition salts. These acid addition salts are formed, for example, with strong inorganic acids, such as mineral acids, for example sulfuric acid, a phosphoric acid or a hydrohalic acid, with strong organic carboxylic acids, such as unsubstituted or substituted, for example halo-substituted, $C_1$–$C_4$alkanecarboxylic acids, for example acetic acid, unsaturated or saturated dicarboxylic acids, for example oxalic acid, malonic acid, maleic acid, fumaric acid or phthalic acid, hydroxycarboxylic acids, for example ascorbic acid, lactic acid, malic acid, tartaric acid or citric acid, or benzoic acid, or with organic sulfonic acids, such as unsubstituted or substituted, for example halo-substituted, $C_1$–$C_4$alkane- or arylsulfonic acids, for example methane- or p-toluene-sulfonic acid. Compounds of formula (I) that have at least one acidic group can furthermore form salts with bases. Suitable salts with bases are, for example, metal salts, such as alkali metal salts or alkaline earth metal salts, for example sodium, potassium or magnesium salts, or salts with ammonia or with an organic amine, such as morpholine, piperidine, pyrrolidine, a mono-, di- or tri-lower alkylamine, for example ethylamine, diethylamine, triethylamine or dimethylpropylamine, or a mono-, di- or trihydroxy-lower alkylamine, for example mono-, di- or tri-ethanolamine. Corresponding internal salts may also be formed where appropriate. The free form is preferred. Among the salts of the compounds of formula (I), the agrochemically advantageous salts are preferred. Hereinbefore and hereinafter, any reference to the free compounds of formula (I) or their salts is to be understood as including, where appropriate, also the corresponding salts or the free compounds of formula (I), respectively. The same applies to tautomers of compounds of formula (I) and salts thereof.

Unless defined otherwise, the general terms used hereinbefore and hereinafter have the meanings given below.

Unless defined otherwise, carbon-containing groups and compounds each contain from 1 up to and including 6, preferably from 1 up to and including 4, especially 1 or 2, carbon atoms.

Halogen—as a group per se and as a structural element of other groups and compounds, such as haloalkyl, haloalkoxy and haloalkylthio—is fluorine, chlorine, bromine or iodine, especially fluorine, chlorine or bromine, more especially fluorine or chlorine.

Alkyl—as a group per se and as a structural element of other groups and compounds, such as haloalkyl, alkoxy and alkylthio—is, in each case giving consideration to the number of carbon atoms contained in the group or compound in question, either straight-chained, i.e. methyl, ethyl, propyl, butyl, pentyl, hexyl, heptyl or octyl, or branched, e.g. isopropyl, isobutyl, sec-butyl, tert-butyl, isopentyl, neopentyl or isohexyl.

Cycloalkyl—as a group per se and as a structural element of other groups and compounds, such as halocycloalkyl, cycloalkoxy and cycloalkylthio—is, in each case giving due consideration to the number of carbon atoms contained in the group or compound in question, cyclopropyl, cyclobutyl, cyclopentyl, cyclohexyl, cycloheptyl or cyclooctyl.

Alkenyl—as a group per se and as a structural element of other groups and compounds—is, in each case giving due consideration to the number of carbon atoms and conjugated or isolated double bonds contained in the group in question, either straight-chained, e.g. vinyl, allyl, 2-butenyl, 3-pentenyl, 1-hexenyl, 1-heptenyl, 1,3-hexadienyl or 1,3-octadienyl, or branched, e.g. isopropenyl, isobutenyl, isoprenyl, tert-pentenyl, isohexenyl, isoheptenyl or isooctenyl. Alkenyl groups having from 3 to 12, especially from 3 to 6, more especially 3 or 4, carbon atoms are preferred.

Alkynyl—as a group per se and as a structural element of other groups and compounds—is, in each case giving due consideration to the number of carbon atoms and conjugated or isolated double bonds contained in the group or compound in question, either straight-chained, e.g. ethynyl, propargyl, 2-butynyl, 3-pentynyl, 1-hexynyl, 1-heptynyl, 3-hexen-1-ynyl or 1,5-heptadien-3-ynyl, or branched, e.g. 3-methylbut-1-ynyl, 4-ethylpent-1-ynyl, 4-methylhex-2-ynyl or 2-methylhept-3-ynyl. Alkynyl groups having from 3 to 12, especially from 3 to 6, more especially 3 or 4, carbon atoms are preferred.

Alkylene and alkenylene are straight-chained or branched bridge members, especially —$CH_2$—$CH_2$—$CH_2$—, —$CH_2$—$CH_2$—$CH_2$—$CH_2$—, —$CH_2$—$CH_2$—$CH_2$—$CH_2$—$CH_2$—, —$CH_2(CH_3)CH_2$—$CH_2$—, —$CH_2C(CH_3)_2$—$CH_2$—, —$CH_2$—CH=CH—$CH_2$—or —$CH_2$—CH=CH—$CH_2$—$CH_2$—.

Halo-substituted carbon-containing groups and compounds, such as alkyl, alkenyl, alkynyl, cycloalkyl, alkoxy or alkylthio substituted by halogen, may be partially halogenated or perhalogenated, it being possible in the case of polyhalogenation for the halogen substituents to be the same or different. Examples of haloalkyl—as a group per se and as a structural element of other groups and compounds, such as haloalkoxy and haloalkylthio—are methyl substituted from one to three times by fluorine, chlorine and/or bromine, such as $CHF_2$ or $CF_3$; ethyl substituted from one to five times by fluorine, chlorine and/or bromine, such as $CH_2CF_3$, $CF_2CF_3$, $CF_2CCl_3$, $CF_2CHCl_2$, $CF_2CHF_2$, $CF_2CFCl_2$, $CF_2CHBr_2$, $CF_2CHClF$, $CF_2CHBrF$ or CClFCHClF; propyl or isopropyl substituted from one to seven times by fluorine, chlorine and/or bromine, such as $CH_2CHBrCH_2Br$, $CF_2CHFCF_3$, $CH_2CF_2CF_3$ or $CH(CF_3)_2$; butyl or an isomer thereof substituted from one to nine times by fluorine, chorine and/or bromine, such as $CF(CF_3)CHFCF_3$ or $CH_2(CF_2)_2CF_3$; pentyl or an isomer thereof substituted from one to eleven times by fluorine, chlorine and/or bromine, such as $CF(CF_3)(CHF)_2CF_3$ or $CH_2(CF_2)_3CF_3$; and hexyl or an isomer thereof substituted from one to thirteen times by fluorine, chlorine and/or bromine, such as $(CH_2)_4CHBrCH_2Br$, $CF_2(CHF)_4CF_3$, $CH_2(CF_2)_4CF_3$ or $C(CF_3)_2(CHF)_2CF_3$.

Aryl is especially phenyl, naphthyl, anthracenyl or perylenyl, preferably phenyl.

Heterocyclyl is especially pyridyl, pyrimidyl, s-triazinyl, 1,2,4-triazinyl, thienyl, furyl, tetrahydrofuranyl, pyranyl, tetrahydropyranyl, pyrrolyl, pyrazolyl, imidazolyl, thiazolyl, triazolyl, tetrazolyl, oxazolyl, thiadiazolyl, oxadiazolyl, benzothienyl, quinolinyl, quinoxalinyl, benzofuranyl, benzimidazolyl, benzopyrrolyl, benzothiazolyl, indolyl, coumarinyl or indazolyl, which are preferably bonded via a carbon atom; preference is given to thienyl, thiazolyl, benzofuranyl, benzothiazolyl, furyl, tetrahydropyranyl and indolyl; especially pyridyl or thiazolyl.

Within the scope of the present invention, preference is given to (2) compounds according to group (1) of formula (I) wherein R, is isopropyl or sec-butyl, preferably wherein a mixture of the isopropyl and the sec-butyl derivative is present;

(3) compounds according to group (2) of formula (I) wherein $R_2$ is H, $C_1$–$C_8$alkyl, $C_1$–$C_8$-alkyl mono- to penta-substituted by halogen, OH or CN; $C_3$–$C_{12}$alkenyl, $C_3$–$C_{12}$alkynyl or $C(O)R_4$;

(4) compounds according to one of groups (1) to (3) of formula (I) wherein $R_2$ is $C_1$–$C_4$alkyl, especially methyl;

(5) compounds according to group (2) of formula (I) wherein $R_2$ is ethyl;

(6) compounds according to group (2) of formula (I) wherein $R_2$ is n-propyl;

(7) compounds according to one of groups (1) to (6) of formula (I) wherein $R_3$ is H, $C_1$–$C_8$alkyl, $C_1$–$C_8$alkyl substituted by halogen, OH or CN; $C_3$–$C_{12}$alkenyl or $C_3$–$C_{12}$alkynyl;

(8) compounds according to one of groups (1) to (6) of formula (I) wherein $R_3$ is H;

(9) compounds according to one of groups (1) to (6) of formula (I) wherein $R_3$ is methyl;

(10) compounds according to one of groups (1) to (6) of formula (I) wherein $R_3$ is ethyl;

(11) compounds according to one of groups (1) to (6) of formula (I) wherein $R_3$ is n-propyl;

(12) compounds according to one of groups (1) to (6) of formula (I) wherein $R_3$ is iso-propyl;

(13) compounds according to one of groups (3) and (7) to (12) of formula (I) wherein $R_4$ is H, OH, $C_1$–$C_4$alkyl, $C_1$–$C_4$alkoxy, halo-$C_1$–$C_4$alkyl, halo-$C_1$–$C_4$alkoxy, $C_3$–$C_8$cycloalkoxy, $C_2$–$C_8$alkenyloxy, $C_2$–$C_8$alkynyloxy, $NH_2$, $NH(C_1$–$C_{12}$alkyl), $N(C_1$–$C_{12}$alkyl)$_2$, aryl, aryloxy, benzyl or benzyloxy; wherein the radicals aryl, aryloxy, benzyl and benzyloxy are unsubstituted or substituted by from one to three substituents selected independently of one another from halogen, $C_1$–$C_4$alkyl, $C_1$–$C_4$haloalkyl, $C_1$–$C_4$alkoxy, $C_1$–$C_4$haloalkoxy, $C_1$–$C_{12}$haloalkylthio, nitro and cyano;

(14) compounds according to one of groups (1) and (2) of formula (I) wherein $R_2$ and $R_3$ together are —$CH_2$—$CH_2$—$CH_2$—or —$CH_2$—$CH_2$—$CH_2$—$CH_2$—;

(15) compounds according to one of groups (1) and (2) of formula (I) wherein $R_2$ and $R_3$ together are —$CH_2$—$CH_2$—O—$CH_2$—$CH_2$—or —$CH_2$—$CH_2$—$N(CH_3)$—$CH_2$—$CH_2$—;

(16) compounds according to one of groups (1) and (7) to (12) of formula (I) wherein $R_2$ is substituted $C_1$–$C_4$alkyl, especially —$CH_2$—, and the substituents are selected from the group consisting of OH, CN, halogen, $C_3$–$C_8$cycloalkyl; $C_3$–$C_8$cycloalkenyl unsubstituted or substituted by from one to three methyl groups; $C_1$–$C_{12}$alkoxy, $C_2$–$C_8$alkynyl, —C(=O)$R_4$, —NHC(=O)$R_6$, —P(=O)(O$C_1$–$C_6$alkyl)$_2$; and phenyl, naphthyl, anthracenyl, phenanthrenyl, fluorenyl, perylenyl and heterocyclyl which are unsubstituted or, depending upon the possibilities of substitution at the ring, mono- to penta-substituted;

especially wherein the substituents of $R_2$ are selected from the group consisting of halogen, CN, $C_3$–$C_8$cycloalkyl, $C_2$–$C_8$alkynyl, —C(=O)$R_4$, —NHC(=O)$R_6$, —P(=O)(O$C_1$–$C_6$alkyl)$_2$; and phenyl, naphthyl, anthracenyl, pyridyl, thiazolyl, imidazolyl, furyl, quinolinyl and pyrazolyl which are unsubstituted or, depending upon the possibilities of substitution at the ring, mono- to tri-substituted;

(17) compounds according to one of groups (1) to (6) and (16) of formula (I) wherein $R_3$ is benzyl that carries on the aromatic moiety from one to three substituents that are selected from the group consisting of OH, halogen, CN, NO$_2$, C$_1$–C$_2$alkyl, dimethylamino-C$_1$–C$_4$alkoxy, C$_3$–C$_6$cycloalkyl, C$_1$–C$_2$haloalkyl, C$_1$–C$_2$alkoxy, C$_1$–C$_2$haloalkoxy, phenoxy, phenyl-C$_1$–C$_6$alkyl, phenyl-C$_1$–C$_4$alkenyl; phenoxy unsubstituted or substituted by chlorine or methoxy; benzyloxy unsubstituted or substituted by chlorine, methoxy or trifluoromethyl; methylenedioxy, —C(=O)R$_5$, —O—C(=O)R$_6$ and NHC(=O)R$_6$;

R$_5$ is H, OH, NH$_2$, NH(C$_1$–C$_2$alkyl), N(C$_1$–C$_2$alkyl)$_2$, —O—C$_1$–C$_2$alkyl-C(=O)—R$_7$, NHC$_1$–C$_2$alkyl-C(=O)—R$_7$, C$_1$–C$_6$alkyl, C$_1$–C$_2$alkoxy, C$_1$–C$_2$alkoxy-C$_1$–C$_2$alkoxy, C$_2$–C$_4$alkenyloxy, C$_2$–C$_4$alkynyloxy; phenyl, phenoxy, benzyloxy, NH-phenyl, NH—C$_1$–C$_6$alkyl-C(=O)—R$_7$; or phenyl, phenoxy, benzyloxy or NH-phenyl substituted by halogen, nitro, methoxy, trifluoromethyl or trifluoromethoxy;

R$_6$ is H, C$_1$–C$_3$alkyl, phenyl or benzyl; and

R$_7$ is H, OH, NH$_2$, NH(C$_1$–C$_{12}$alkyl), N(C$_1$–C$_{12}$alkyl)$_2$, C$_1$–C$_{12}$alkyl, C$_1$–C$_{12}$alkoxy, C$_1$–C$_6$alkoxy-C$_1$–C$_6$alkoxy, C$_2$–C$_8$alkenyloxy, phenyl, phenoxy, benzyloxy or NH-phenyl;

(18) compounds according to one of groups (1) to (6) of formula (I) wherein R$_3$ is C$_1$–C$_4$alkyl-C(=O)R$_5$, especially —CH$_2$—C(=O)R$_5$; and R$_5$ is H, OH, NH$_2$, NH(C$_1$–C$_2$alkyl), N(C$_1$–C$_2$alkyl)$_2$, C$_1$–C$_4$alkyl, C$_1$–C$_{12}$alkoxy, C$_2$–C$_4$alkenyloxy, phenyl, phenoxy, benzyloxy, NH-phenyl, NH—C$_1$–C$_2$alkyl-C(=O)—O—C$_1$–C$_2$-alkyl-phenyl, —P(=O)(OC$_1$–C$_6$alkyl)$_2$; or phenyl, phenoxy, benzyloxy or NH-phenyl substituted by chlorine, fluorine, methoxy, trifluoromethyl or trifluoromethoxy;

more especially wherein R$_5$ is C$_1$–C$_{12}$alkoxy;

(19) compounds according to one of groups (1) to (6) of formula (I) wherein R$_4$ is unsubstituted benzyl;

(20) compounds according to one of groups (1) to (19) of formula (I) that have the R configuration at the 4"-position;

(21) compounds according to one of groups (1) to (19) of formula (I) that have the S configuration at the 4"-position.

Special preference is given within the scope of the invention to compounds P.1 to P.17 and to the compounds of formula (I) listed in Tables 1 to 3 and, where applicable, their E/Z isomers and mixtures of E/Z isomers.

The invention further relates to a process for the preparation of the compounds of formula (I) as defined above under (1) and, where applicable, tautomers thereof, which comprises (A) reacting a compound of formula:

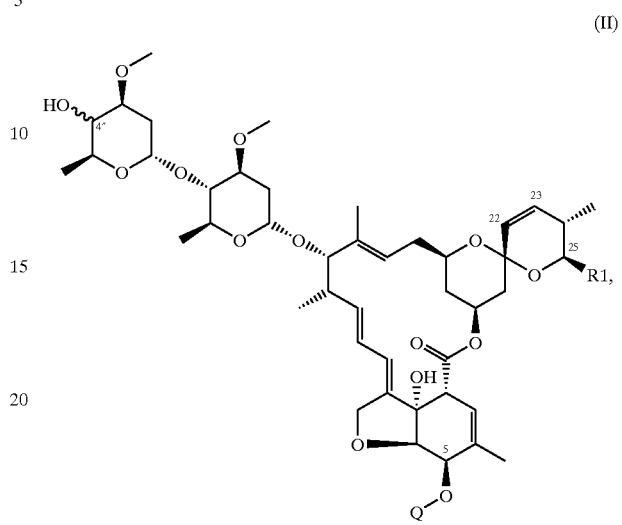

wherein the bond marked by ∼ indicates the S- as well as the R-isomer at the 4"-position; wherein R$_1$ is as defined above under (1) for formula (I) and Q is a protecting group, and which is known or can be prepared by methods known per se, with a compound of formula:

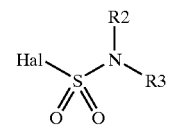

wherein R$_2$ and R$_3$ are as defined above for formula (I) and Hal is a halogen atom, preferably bromine or iodine, and which is known or can be prepared by methods known per se, to form a compound of formula:

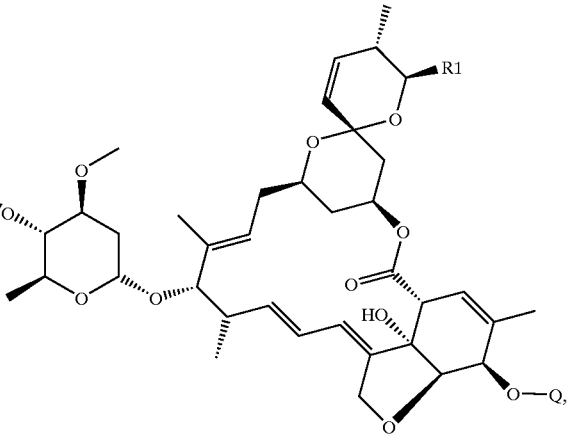

wherein Q, $R_1$, $R_2$ and $R_3$ are as defined for formula (II); and (B) removing the protecting group Q of the compound of formula (IV) so obtained; or (C) reacting a compound of formula (I) wherein $R_1$ and $R_3$ are as defined for formula (I) and $R_2$ is H, with a compound of the formula Hal-$R_2$ wherein $R_2$ is as defined for formula (I) and Hal is halogen, especially bromine or iodine; or (D) reacting a compound of formula (IV) wherein Q, $R_1$ and $R_3$ are as defined for formula (IV) and $R_2$ is H, with a compound of the formula Hal-$R_2$ wherein $R_2$ is as defined for formula (I) and Hal is halogen, especially bromine or iodine; and removing the protecting group Q from the compound of formula (IV) so obtained analogously to process step (B); or (E) for the preparation of a compound of formula (I) wherein $R_1$ is as defined for formula (I) and $R_2$ and $R_3$ are identical and, with the exception of hydrogen, are as defined for formula (I), reacting a compound of formula (I) wherein $R_1$ is as defined for formula (I) and $R_2$ and $R_3$ are H, with two moles of a compound of the formula Hal-$R_2$ wherein $R_2$ is as defined for formula (I) and Hal is halogen, especially bromine or iodine; or reacting a compound of formula (IV) wherein $R_1$ is as defined for formula (IV) and $R_2$ and $R_3$ are H, with two moles of a compound of the formula Hal-$R_2$ wherein $R_2$ is as defined for formula (I) and Hal is halogen, especially bromine or iodine; and then removing the protecting group Q analogously to process step (B); or (F) for the preparation of a compound of formula (I) wherein $R_1$ is as defined for formula (I) and $R_2$ and $R_3$ together are a three- to seven-membered alkylene bridge or a four- to seven-membered alkenylene bridge wherein one $CH_2$ group in the alkylene or alkenylene may have been replaced by O, S or $NR_5$, reacting a compound of formula (I) wherein $R_1$ is as defined for formula (I) and $R_2$ and $R_3$ are H, with one mole of a compound of the formula Hal-A-Hal wherein the bridge member A has the above-mentioned definition of $R_2$ and $R_3$ together and Hal is halogen, especially bromine or iodine; or, analogously to process step (E), reacting a compound of formula (IV) wherein $R_1$ and Q are as defined for formula (IV) and $R_2$ and $R_3$ are H, with one mole of a compound of the formula Hal-A-Hal as defined above, and then removing the protecting group Q analogously to process step (B); or (G) for the preparation of a compound of formula (I) wherein $R_2$ is —C(O)$R_4$ and $R_1$, $R_3$ and $R_4$ are as defined for formula (I), either reacting a compound of formula (I) wherein $R_1$ and $R_3$ are as defined for formula (I) and $R_2$ is H, with a compound of the formula Hal-C(O)$R_4$ wherein $R_4$ is as defined above for formula (I) and Hal is halogen; or reacting a compound of formula (IV) wherein $R_1$, $R_3$, $R_4$ and Q are as defined for formula (I) and $R_2$ is H, with a compound of the formula Hal-C(O)$R_4$ wherein $R_4$ is as defined above for formula (I) and Hal is halogen; and then removing the protecting group Q.

The remarks made above regarding tautomers of compounds of formula (I) apply analogously to the starting materials mentioned hereinbefore and hereinafter with regard to their tautomers.

The reactions described hereinbefore and hereinafter are carried out in a manner known per se, for example in the absence or, customarily, in the presence of a suitable solvent or diluent or of a mixture thereof, the reactions being carried out, as required, with cooling, at room temperature or with heating, for example in a temperature range of approximately from −80° C. to the boiling temperature of the reaction medium, preferably from approximately 0° C. to approximately +150° C., and, if necessary, in a closed vessel, under pressure, under an inert gas atmosphere and/or under anhydrous conditions. Especially advantageous reaction conditions can be found in the Examples.

The reaction time is not critical; a reaction time of from approximately 0.1 to approximately 72 hours, especially from approximately 0.5 to approximately 24 hours, is preferred.

The product is isolated by customary methods, for example by means of filtration, crystallisation, distillation or chromatography, or any suitable combination of such methods.

The starting materials mentioned hereinbefore and hereinafter that are used for the preparation of the compounds of formula (I) and, where applicable, their tautomers are known or can be prepared by methods known per se, e.g. as indicated below.

The starting materials of formula:

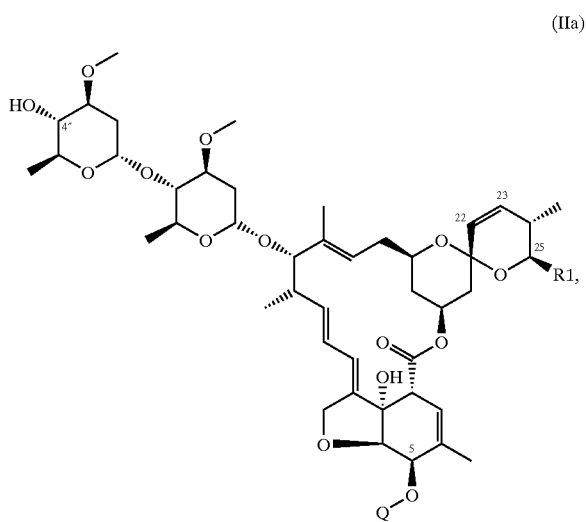

(IIa)

and the compounds of formula:

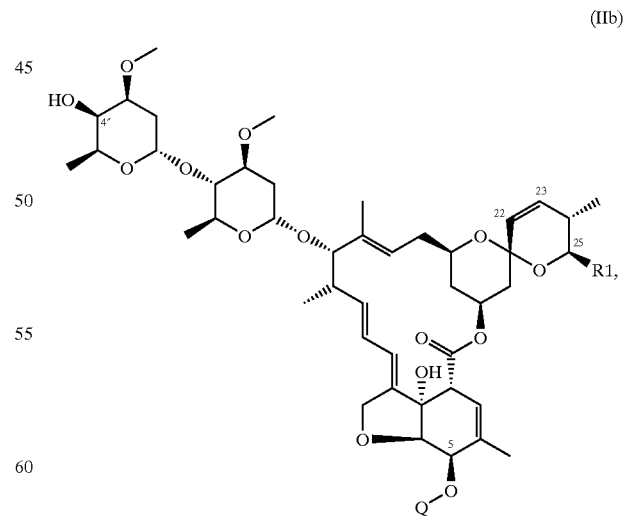

(IIb)

wherein $R_1$ and Q are as defined above are known to the person skilled in the art (abamectin B1a or 4"-epi-abamectin B1a each provided with a protecting group in the 5-position) or can be prepared by methods known per se.

Process Variant (A):

Examples of solvents and diluents include: aromatic, aliphatic and alicyclic hydrocarbons and halogenated hydrocarbons, such as benzene, toluene, xylene, mesitylene, tetralin, chlorobenzene, dichlorobenzene, bromobenzene, petroleum ether, hexane, cyclohexane, dichloromethane, trichloromethane, tetrachloromethane, dichloroethane, trichloroethene or tetrachloroethene; ethers, such as diethyl ether, dipropyl ether, diisopropyl ether, dibutyl ether, tert-butyl methyl ether, ethylene glycol monomethyl ether, ethylene glycol monoethyl ether, ethylene glycol dimethyl ether, dimethoxydiethyl ether, tetrahydrofuran or dioxane; esters of carboxylic acids, such as ethyl acetate; amides, such as dimethylformamide, dimethylacetamide or 1-methyl-2-pyrrolidinones; nitriles, such as acetonitrile; sulfoxides, such as dimethyl sulfoxide; or mixtures of the mentioned solvents. Preference is given to amides, such as dimethylformamide and dimethylacetamide, especially dimethylacetamide.

Protecting groups Q in the compounds of formulae (II) and (IV) include: alkyl ether radicals, such as methoxymethyl, methylthiomethyl, tert-butylthiomethyl, benzyloxymethyl, p-methoxybenzyl, 2-methoxyethoxymethyl, 2,2,2-trichloroethoxymethyl, 2-(trimethylsilyl)ethoxymethyl, tetrahydropyranyl, tetrahydrofuranyl, 1-ethoxyethyl, 1-(2-chloroethoxy)ethyl, 1-methyl-1-methoxyethyl, 1-methyl-1-benzyloxyethyl, trichloroethyl, 2-trimethylsilylethyl, tert-butyl, allyl, p-methoxyphenyl, 2,4-dinitrophenyl, benzyl, p-methoxybenzyl, o-nitrobenzyl, p-nitrobenzyl, triphenylmethyl; trialkylsilyl radicals, such as trimethylsilyl, triethylsilyl, dimethyl-tert-butylsilyl, dimethylisopropylsilyl, dimethyl-1,1,2-trimethylpropylsilyl, diethylisopropylsilyl, dimethyl-tert-hexylsilyl, but also phenyl-tert-alkylsilyl groups, such as diphenyl-tert-butylsilyl; esters, such as formates, acetates, chloroacetates, dichloroacetates, trichloroacetates, trifluoroacetates, methoxyacetates, phenoxyacetates, pivaloates, benzoates; alkyl carbonates, such as methyl-, 9-fluorenylmethyl-, ethyl-, 2,2,2-trichloroethyl-, 2-(trimethylsilyl)ethyl-, vinyl-, allyl-, benzyl-, p-methoxybenzyl-, o-nitrobenzyl-, p-nitrobenzyl-, but also p-nitrophenyl-carbonate.

Preference is given to trialkylsilyl radicals, such as trimethylsilyl, triethylsilyl, dimethyl-tert-butylsilyl, diphenyl-tert-butylsilyl, esters, such as methoxyacetates and phenoxyacetates, and carbonates, such as 9-fluorenylmethylcarbonates and allylcarbonates. Dimethyl-tert-butylsilyl ether is especially preferred.

The reactions are advantageously carried out in a temperature range of from approximately −70° C. to 50° C., preferably at from −10° C. to 25° C.

Especially preferred conditions for the reaction are described in Example P.1.

Process Variant (B):

Examples of solvents and diluents are the same as those mentioned under Process variant A. In addition, alcohols, such as methanol, ethanol or 2-propanol, and water are suitable.

The reactions are advantageously carried out in a temperature range of approximately from −70° C. to 100° C., preferably at from −10° C. to 25° C.

There are suitable for the removal of the protecting group Lewis acids, such as hydrochloric acid, methanesulfonic acid, $BF_3*OEt_2$, HF in pyridine, $Zn(BF_4)_2*H_2O$, p-toluenesulfonic acid, $AlCl_3$, $HgCl_2$; ammonium fluoride, such as tetrabutylammonium fluoride; bases, such as ammonia, trialkylamine or heterocyclic bases; hydrogenolysis with a catalyst, such as palladium-on-carbon; reducing agents, such as sodium borohydride or tributyltin hydride with a catalyst, such as $Pd(PPh_3)_4$, or also zinc with acetic acid.

Preference is given to acids, such as methanesulfonic acid or HF in pyridine; sodium borohydride with Pd(0); bases, such as ammonia, triethylamine or pyridine; especially acids, such as HF in pyridine or methanesulfonic acid.

Especially preferred conditions for the reaction are described in Example P.1.

Process Variant (C):

Examples of solvents and diluents are the same as those mentioned under Process variant (A). In addition, alcohols, such as methanol, ethanol or 2-propanol, are suitable. Preference is given to amides, such as dimethylformamide, and nitriles, such as acetonitrile; especially acetonitrile.

The reactions are advantageously carried out in a temperature range of approximately from −10° C. to 120° C., preferably at from 20° C. to 100° C.

Suitable bases are especially carbonates, such as sodium carbonate, sodium hydrogen carbonate, potassium carbonate, trialkylamines, such as triethylamine, and heterocyclic bases, such as pyridine.

Especially preferred conditions for the reaction are described in Example P.4.

Process variants (D) to (F) are carried out substantially analogously to Process variant (C).

Process Variant (G):

Examples of solvents and diluents are the same as those mentioned under Process variant (B).

Ethyl acetate and water are preferred.

The reactions are advantageously carried out in a temperature range of approximately from −10° C. to 120° C., preferably at from 20° C. to 80° C.

Suitable bases are especially carbonates, such as sodium carbonate, sodium hydrogen carbonate, potassium carbonate, trialkylamines, such as triethylamine, and heterocyclic bases, such as pyridine.

Especially preferred conditions for the reaction are described in Example P.11.

The compounds of formula (I) may be in the form of one of the possible isomers or in the form of a mixture thereof, in the form of pure isomers or in the form of an isomeric mixture, i.e. in the form of a racemic mixture; the invention relates both to the pure isomers and to the racemic mixtures and is to be interpreted accordingly hereinbefore and hereinafter, even if stereochemical details are not mentioned specifically in every case.

The racemates can be resolved into the optical antipodes by known methods, for example by recrystallisation from an optically active solvent, by chromatography on chiral adsorbents, for example high pressure liquid chromatography (HPLC) on acetylcellulose, with the aid of suitable microorganisms, by cleavage with specific, immobilised enzymes, or via the formation of inclusion compounds, for example using chiral crown ethers, only one isomer being complexed.

Apart from by separation of corresponding mixtures of isomers, pure optical isomers can be obtained according to the invention also by generally known methods of enantioselective synthesis, for example by carrying out the process according to the invention using starting materials having correspondingly suitable stereochemistry.

In each case it is advantageous to isolate or synthesise the biologically more active isomer, where the individual components have different biological activity.

The compounds of formula (I) may also be obtained in the form of their hydrates and/or may include other solvents, for example solvents which may have been used for the crystallisation of compounds in solid form.

The invention relates to all those embodiments of the process according to which a compound obtainable as starting material or intermediate at any stage of the process is used as starting material and some or all of the remaining steps are carried out or a starting material is used in the form of a derivative or salt and/or its racemates or antipodes or, especially, is formed under the reaction conditions.

In the processes of the present invention it is preferable to use those starting materials and intermediates which result in the compounds of formula (I) that are especially preferred.

The invention relates especially to the preparation processes described in the Examples.

The invention further relates to the compounds of formula (IV) and, where applicable, E/Z isomers, mixtures of E/Z isomers and/or tautomers, in each case in free form or in salt form.

In the area of pest control, the compounds of formula (I) according to the invention are active ingredients exhibiting valuable preventive and/or curative activity with a very advantageous biocidal spectrum and a very broad spectrum, even at low rates of concentration, while being well tolerated by warm-blooded animals, fish and plants. They are, surprisingly, equally suitable for controlling both plant pests and ecto- and endo-parasites in humans and more especially in productive livestock, domestic animals and pets. They are effective against all or individual development stages of normally sensitive animal pests, but also of resistant animal pests, such as insects and representatives of the order Acarina, nematodes, cestodes and trematodes, while at the same time protecting useful organisms. The insecticidal or acaricidal activity of the active ingredients according to the invention may manifest itself directly, i.e. in the mortality of the pests, which occurs immediately or only after some time, for example during moulting, or indirectly, for example in reduced oviposition and/or hatching rate, good activity corresponding to a mortality of at least 50 to 60%.

The action of the compounds according to the invention and the compositions comprising them against animal pests can be significantly broadened and adapted to the given circumstances by the addition of other insecticides, acaricides or nematicides. Suitable additives include, for example, representatives of the following classes of active ingredient: organophosphorus compounds, nitrophenols and derivatives, formamidines, ureas, carbamates, pyrethroids, chlorinated hydrocarbons, neonicotinoids and Bacillus thuringiensis preparations.

Examples of especially suitable mixing partners include: azamethiphos; chlorfenvinphos; cypermethrin, cypermethrin high-cis; cyromazine; diafenthiuron; diazinon; dichlorvos; dicrotophos; dicyclanil; fenoxycarb; fluazuron; furathiocarb; isazofos; iodfenphos; kinoprene; lufenuron; methacriphos; methidathion; monocrotophos; phosphamidon; profenofos; diofenolan; a compound obtainable from the Bacillus thuringiensis strain GC91 or from strain NCTC11821; pymetrozine; bromopropylate; methoprene; disulfoton; quinalphos; taufluvalinate; thiocyclam; thiometon; aldicarb; azinphos-methyl; benfuracarb; bifenthrin; buprofezin; carbofuran; dibutylaminothio; cartap; chlorfluazuron; chlorpyrifos; cyfluthrin; lambda-cyhalothrin; alpha-cypermethrin; zeta-cypermethrin; deltamethrin; diflubenzuron; endosulfan; ethiofencarb; fenitrothion; fenobucarb; fenvalerate; formothion; methiocarb; heptenophos; imidacloprid; isoprocarb; methamidophos; methomyl; mevinphos; parathion; parathion-methyl; phosalone; pirimicarb; propoxur; teflubenzuron; terbufos; triazamate; fenobucarb; tebufenozide; fipronil; beta-cyfluthrin; silafluofen; fenpyroximate; pyridaben; fenazaquin; pyriproxyfen; pyrimidifen; nitenpyram; acetamiprid; emamectin; emamectinbenzoate; spinosad; a plant extract that is active against insects; a preparation that comprises nematodes and is active against insects; a preparation obtainable from *Bacillus subtilis*; a preparation that comprises fungi and is active against insects; a preparation that comprises viruses and is active against insects; chlorfenapyr; acephate; acrinathrin; alanycarb; alphamethrin; amitraz; AZ 60541; azinphos A; azinphos M; azocyclotin; bendiocarb; bensultap; beta-cyfluthrin; BPMC; brofenprox; bromophos A; bufencarb; butocarboxin; butylpyridaben; cadusafos; carbaryl; carbophenothion; chloethocarb; chlorethoxyfos; chlormephos; cis-resmethrin; clocythrin; clofentezine; cyanophos; cycloprothrin; cyhexatin; demeton M; demeton S; demeton-S-methyl; dichlofenthion; dicliphos; diethion; dimethoate; dimethylvinphos; dioxathion; edifenphos; esfenvalerate; ethion; ethofenprox; ethoprophos; etrimphos; fenamiphos; fenbutatin oxide; fenothiocarb; fenpropathrin; fenpyrad; fenthion; fluazinam; flucycloxuron; flucythrinate; flufenoxuron; flufenprox; fonophos; fosthiazate; fubfenprox; HCH; hexaflumuron; hexythiazox; IKI-220; iprobenfos; isofenphos; isoxathion; ivermectin; malathion; mecarbam; mesulfenphos; metaldehyde; metolcarb; milbemectin; moxidectin; naled; NC 184; omethoate; oxamyl; oxydemethon M; oxydeprofos; permethrin; phenthoate; phorate; phosmet; phoxim; pirimiphos M; pirimiphos E; promecarb; propaphos; prothiofos; prothoate; pyrachlophos; pyradaphenthion; pyresmethrin; pyrethrum; tebufenozide; salithion; sebufos; sulfotep; sulprofos; tebufenpyrad; tebupirimphos; tefluthrin; temephos; terbam; tetrachlorvinphos; thiacloprid; thiafenox; thiodicarb; thiofanox; thionazin; thuringiensin; tralomethrin; triarthene; triazophos; triazuron; trichlorfon; triflumuron; trimethacarb; vamidothion; xylylcarb; YI 5301/5302; zetamethrin; DPX-MP062—indoxacarb; methoxyfenozide; bifenazate; XMC (3,5-xylyl methylcarbamate); or the fungus pathogen *Metarhizium anisopliae*; most especially fipronil, thiamethoxam, or lambda-cyhalothrin.

The said animal pests include, for example, those mentioned in European Patent Application EP-A-736 252, page 5, line 55, to page 6, line 55. The pests mentioned therein are therefore included by reference in the subject matter of the present invention.

It is also possible to control pests of the class Nematoda using the compounds according to the invention. Such pests include, for example, root knot nematodes, cyst-forming nematodes and also stem and leaf nematodes;

especially of *Heterodera* spp., e.g. *Heterodera schachtii*, *Heterodora avenae* and *Heterodora trifolii*; *Globodera* spp., e.g. *Globodera rostochiensis*; *Meloidogyne* spp., e.g. *Meloidogyne incognita* and *Meloidogyne javanica*; *Radopholus* spp., e.g. *Radopholus similis*; *Pratylenchus*, e.g. *Pratylenchus neglectans* and *Pratylenchus penetrans*; *Tylenchulus*, e.g. *Tylenchulus semipenetrans*; *Longidorus, Trichodorus, Xiphinema, Ditylenchus, Apheenchoides* and *Anguina*; especially *Meloidogyne*, e.g. *Meloidogyne incognita*, and *Heterodera*, e.g. *Heterodera glycines*.

An especially important aspect of the present invention is the use of the compounds of formula (I) according to the invention in the protection of plants against parasitic feeding pests.

The compounds according to the invention can be used to control, i.e. to inhibit or destroy, pests of the mentioned type occurring on plants, especially on useful plants and ornamentals in agriculture, in horticulture and in forestry, or on parts of such plants, such as the fruits, blossoms, leaves, stems, tubers or roots, while in some cases plant parts that grow later are still protected against those pests.

Target crops include especially cereals, such as wheat, barley, rye, oats, rice, maize and sorghum; beet, such as sugar beet and fodder beet; fruit, e.g. pomes, stone fruit and soft fruit, such as apples, pears, plums, peaches, almonds, cherries and berries, e.g. strawberries, raspberries and blackberries; leguminous plants, such as beans, lentils, peas and soybeans; oil plants, such as rape, mustard, poppy, olives, sunflowers, coconut, castor oil, cocoa and groundnuts; cucurbitaceae, such as marrows, cucumbers and melons; fibre plants, such as cotton, flax, hemp and jute; citrus fruits, such as oranges, lemons, grapefruit and mandarins; vegetables, such as spinach, lettuce, asparagus, cabbages, carrots, onions, tomatoes, potatoes and paprika; lauraceae, such as avocado, cinnamon and camphor; and tobacco, nuts, coffee, aubergines, sugar cane, tea, pepper, vines, hops, bananas, natural rubber plants and ornamentals.

Further areas of use of the compounds according to the invention are the protection of stored goods and storerooms and the protection of raw materials, and also in the hygiene sector, especially the protection of domestic animals and productive livestock against pests of the mentioned type, more especially the protection of domestic animals, especially cats and dogs, from infestation by fleas, ticks and nematodes.

The invention therefore relates also to pesticidal compositions, such as emulsifiable concentrates, suspension concentrates, directly sprayable or dilutable solutions, spreadable pastes, dilute emulsions, wettable powders, soluble powders, dispersible powders, wettable powders, dusts, granules and encapsulations of polymer substances, that comprise at least one of the compounds according to the invention, the choice of formulation being made in accordance with the intended objectives and the prevailing circumstances.

The active ingredient is used in those compositions in pure form, a solid active ingredient, for example, in a specific particle size, or preferably together with at least one of the adjuvants customary in formulation technology, such as extenders, e.g. solvents or solid carriers, or surface-active compounds (surfactants). In the area of parasite control in humans, domestic animals, productive livestock and pets it will be self-evident that only physiologically tolerable additives are used.

As formulation adjuvants there are used, for example, solid carriers, solvents, stabilisers, "slow release" adjuvants, colourings and optionally surface-active substances (surfactants). Suitable carriers and adjuvants include all substances customarily used. As adjuvants, such as solvents, solid carriers, surface-active compounds, non-ionic surfactants, cationic surfactants, anionic surfactants and further adjuvants in the compositions used according to the invention, there come into consideration, for example, those described in EP-A-736 252, page 7, line 51 to page 8, line 39.

The compositions for use in crop protection and in humans, domestic animals and productive livestock generally comprise from 0.1 to 99%, especially from 0.1 to 95%, of active ingredient and from 1 to 99.9%, especially from 5 to 99.9%, of at least one solid or liquid adjuvant, the composition generally including from 0 to 25%, especially from 0.1 to 20%, of surfactants (% =% by weight in each case). Whereas commercial products will preferably be formulated as concentrates, the end user will normally employ dilute formulations having considerably lower concentrations of active ingredient.

Preferred crop protection products have especially the following compositions (%=percent by weight):

| Emulsifiable concentrates: | |
|---|---|
| active ingredient: | 1 to 90%, preferably 5 to 20% |
| surfactant: | 1 to 30%, preferably 10 to 20% |
| solvent: | 5 to 98%, preferably 70 to 85% |
| Dusts: | |
| active ingredient: | 0.1 to 10%, preferably 0.1 to 1% |
| solid carrier: | 99.9 to 90%, preferably 99.9 to 99% |
| Suspension concentrates: | |
| active ingredient: | 5 to 75%, preferably 10 to 50% |
| water: | 94 to 24%, preferably 88 to 30% |
| surfactant: | 1 to 40%, preferably 2 to 30% |
| Wettable powders: | |
| active ingredient: | 0.5 to 90%, preferably 1 to 80% |
| surfactant: | 0.5 to 20%, preferably 1 to 15% |
| solid carrier: | 5 to 99%, preferably 15 to 98% |
| Granules: | |
| active ingredient: | 0.5 to 30%, preferably 3 to 15% |
| solid carrier: | 99.5 to 70%, preferably 97 to 85% |

The compositions according to the invention may also comprise further solid or liquid adjuvants, such as stabilisers, e.g. vegetable oils or epoxidised vegetable oils (e.g. epoxidised coconut oil, rapeseed oil or soybean oil), antifoams, e.g. silicone oil, preservatives, viscosity regulators, binders and/or tackifiers as well as fertilisers or other active ingredients for obtaining special effects, e.g. acaricides, bactericides, fungicides, nematicides, molluscicides or selective herbicides.

The crop protection products according to the invention are prepared in known manner, in the absence of adjuvants, e.g. by grinding, sieving and/or compressing a solid active ingredient or mixture of active ingredients, for example to a certain particle size, and in the presence of at least one adjuvant, for example by intimately mixing and/or grinding the active ingredient or mixture of active ingredients with the adjuvant(s). The invention relates likewise to those processes for the preparation of the compositions according to the invention and to the use of the compounds of formula (I) in the preparation of those compositions.

The invention relates also to the methods of application of the crop protection products, i.e. the methods of controlling pests of the mentioned type, such as spraying, atomising, dusting, coating, dressing, scattering or pouring, which are selected in accordance with the intended objectives and the prevailing circumstances, and to the use of the compositions for controlling pests of the mentioned type. Typical rates of concentration are from 0.1 to 1000 ppm, preferably from 0.1 to 500 ppm, of active ingredient. The rates of application per hectare are generally from 1 to 2000 g of active ingredient per hectare, especially from 10 to 1000 g/ha, preferably from 20 to 600 g/ha.

A preferred method of application in the area of crop protection is application to the foliage of the plants (foliar application), the frequency and the rate of application being dependent upon the risk of infestation by the pest in question. However, the active ingredient can also penetrate the plants through the roots (systemic action) when the locus of the plants is impregnated with a liquid formulation or when the active ingredient is incorporated in solid form into the locus of the plants, for example into the soil, e.g. in granular form (soil application). In the case of paddy rice crops, such granules may be applied in metered amounts to the flooded rice field.

The crop protection products according to the invention are also suitable for protecting plant propagation material, e.g. seed, such as fruits, tubers or grains, or plant cuttings, against animal pests. The propagation material can be treated with the composition before planting: seed, for example, can be dressed before being sown. The active ingredients according to the invention can also be applied to grains (coating), either by impregnating the seeds in a liquid formulation or by coating them with a solid formulation. The composition can also be applied to the planting site when the propagation material is being planted, for example to the seed furrow during sowing. The invention relates also to such methods of treating plant propagation material and to the plant propagation material so treated.

PREPARATION EXAMPLES

In the following Examples, the preparation of avermectin B1 derivatives (mixtures of avermectin B1a and B1b derivative) is described. The B1b derivative generally represents about only from 5 to 10% by weight of the mixtures and, for that reason, usually only the bands of the B1a derivative can be detected in the NMR spectrum.

Since the compounds are in most cases in the form of mixtures of the avermectin B1a and B1b derivative, characterisation by means of the customary physical data such as melting point or refractive index is of little use. For that reason, the compounds are characterised by means of NMR spectroscopy following purification by chromatography, or by reference to the retention times determined in analysis by means of HPLC (high-resolution liquid chromatography). The term "B1a" in the physical data on the Preparation Examples refers to the main component, wherein $R_1$ is sec-butyl. "B1b" represents the secondary component, wherein R. is isopropyl. In the case of the compounds for which a retention time is given only for the B1a derivative, it is not possible to determine the retention time for the B1b component owing to the small proportion of B1b derivative.

Allocation of the correct structures of the B1a and B1b components is carried out by mass spectrometry.

The following method is used for the HPLC analysis:

| HPLC gradient conditions | | | |
|---|---|---|---|
| solvent A: | 0.01% trifluoroacetic acid in $H_2O$ | | |
| solvent B: | 0.01% trifluoroacetic acid in $CH_3CN$ | | |
| time [min] | A [%] | B [%] | flow rate [μl/min] |
| 0 | 80 | 20 | 500 |
| 0.1 | 50 | 50 | 500 |
| 10 | 5 | 95 | 500 |
| 15 | 0 | 100 | 500 |
| 17 | 0 | 100 | 500 |
| 17.1 | 80 | 20 | 500 |
| 22 | 80 | 20 | 500 |
| column: | YMC-Pack ODS-AQ | | |
| column length: | 125 mm | | |
| column internal diameter: | 2 mm | | |
| temperature: | 40° C. | | |

The YMC-Pack ODS-AQ column used for chromatography of the compounds is produced by YMC, Alte Raesfelderstrasse 6, 46514 Schermbeck, Germany.

The abbreviations used in the physical data information have the following meanings:

s: singlet, MHz: megahertz, brs: broad singlet; t: triplet; m: multiplet; d: doublet; J: coupling constant; bd: broad doublet; LCMS: liquid chromatography mass spectrometry; tRT: retention time in minutes; M+H: mass peak plus H; M+Na: mass peak plus Na. TBDMS in the Examples represents the radical —$Si(CH_3)_2$(tert-butyl). Mixing ratios of solvents are given in parts by volume. "Ether" is understood to mean diethyl ether.

Example P.1

Preparation of 4"-sulfamoyloxy-avermectin $B_1$

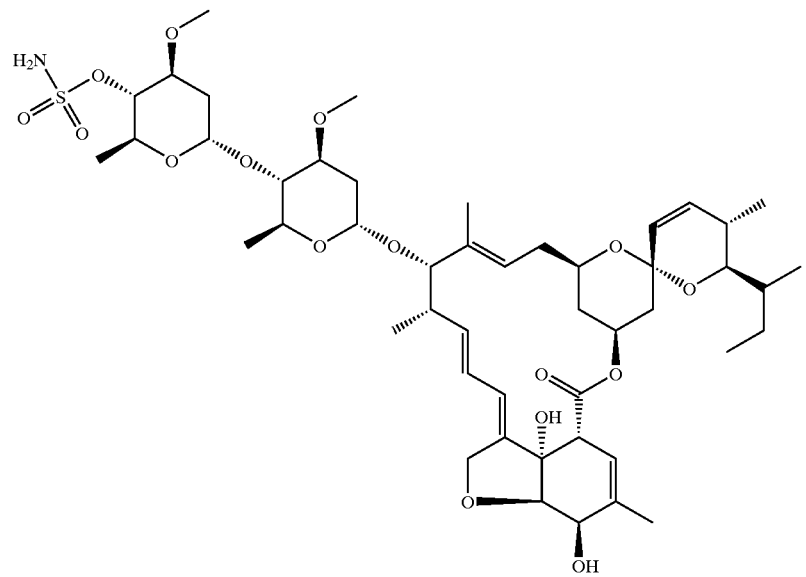

Preparation of sulfamoyl chloride ($ClSO_2NH_2$): 15.5 ml of formic acid are added dropwise at −10° C. to 35 ml of chlorosulfonyl isocyanate and the temperature is maintained below +10° C. by cooling with ice. At the end of the addition, stirring is continued at room temperature until the evolution of gas ceases. The mixture is taken up in benzene, filtered, and concentrated by evaporation in vacuo, yielding the desired sulfamoyl chloride.

Step A: 3.51 g of sulfamoyl chloride are added in portions at −10° C. to a solution of 15 g of 5-O-TBDMS-avermectin $B_1$ in 90 ml of dimethylacetamide under argon. The mixture is allowed to warm to room temperature and is stirred for a further hour. The mixture is poured onto saturated aqueous NaCl solution, extracted twice with tert-butyl methyl ether, dried over $Na_2SO_4$ and concentrated by evaporation, yielding the desired intermediate 5-O-TBDMS-4"-O-sulfamoyloxy-avermectin $B_1$.

Step B: The crude product from Step A is dissolved in 75 ml of methanol. Then, at −5° C., 1.5 ml of methanesulfonic acid in 75 ml of methanol are added dropwise in the course of one hour. The mixture is allowed to warm to room temperature and is left to react for four hours. The solution is poured onto saturated aqueous $NaHCO_3$ solution, concentrated by evaporation in vacuo, and extracted twice with tert-butyl methyl ether. Washing with saturated aqueous NaCl solution, drying over $Na_2SO_4$ and concentration by evaporation yield the crude product. Flash column chromatography on silica gel in $CH_2Cl_2$/ethyl acetate (9:1) yields the desired product in the form of a colourless foam.

4"-Sulfamoyloxy-avermectin $B_1$: $C_{48}H_{73}NO_{16}S$, molecular weight: 951.5. LCMS: $t_{RT}$, $B_{1a}$: 9.08 min., 974.5 (M+Na), 952.5 (M+H), $B_{1b}$: 8.44 min.; NMR (250 MHz, $CDCl_3$) selected data, δH (ppm): 1.48 (s, 3H, $CH_3$-14a), 1.86 (s, 3H, $CH_3$-4a), 3.21 (t, 1H, J=9.2 Hz, CH-4'), 3.28 (m, 1H, CH-2), 3.40 (s, 3H, $OCH_3$), 3.42 (s, 3H, $OCH_3$), 3.95 (d, 1H, J=6.4 Hz, CH-6), 4.05 (s, 1H, HO—C-7), 4.14 (t, 1H, J=9.6 Hz, CH-4"), 4.28 (m, 1H, CH-5), 4.67 (m, 2H, $CH_2$-8a), 4.76 (d, 1H, J=2.75 Hz, CH-1'), 4.96 (m, 1H, CH-15), 5.10 (brs, 2H, $H_2NSO_2OC$-4").

Example P.2

Preparation of 4"-methylaminosulfonyloxy-avermectin $B_1$

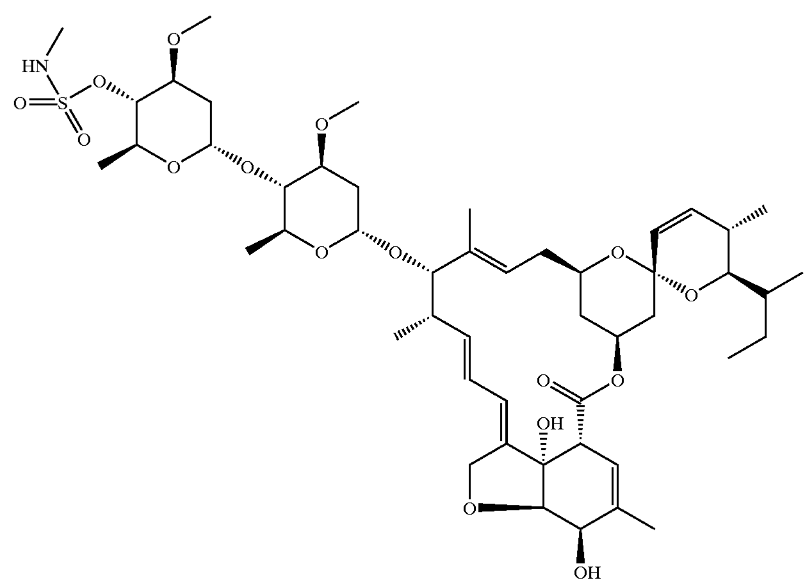

Preparation of N-methylsulfamoyl chloride (ClSO$_2$NHMe): 16.9 g of methylamine hydrochloride in 80 ml of acetonitrile are added to a solution of 65 ml of sulfuryl chloride in 50 ml of acetonitrile. After 24 hours at 60° C., the reaction mixture is cooled to room temperature, filtered off and concentrated by evaporation. Vacuum distillation of the resulting brown oil yields the desired product in the form of a colourless oil.

Step A: 240 mg of N-methylsulfamoyl chloride are added at 0° C. to a solution of 400 mg of 5-O-TBDMS-avermectin B$_1$ in 5 ml of dimethylacetamide under argon, and the mixture is left to react at room temperature for 2 hours. The mixture is poured onto saturated NaCl solution, extracted twice with ethyl acetate, dried over Na$_2$SO$_4$ and concentrated by evaporation, yielding the desired intermediate 5-O-TBDMS-4"-O-(N-methyl)-sulfamoyloxy-avermectin B$_1$.

Step B: 1 ml of HF-pyridine reagent (25 g of commercial 70% HF-pyridine solution, 27.5 ml of tetrahydrofuran, 12.5 ml of pyridine) is added to a solution of the resulting crude product in 5 ml of absolute tetrahydrofuran and the mixture is left to stand at room temperature for 12 hours. The reaction mixture is poured onto water and is extracted twice with ether. Washing with saturated NaHCO$_3$ solution, drying over Na$_2$SO$_4$ and concentration by evaporation yield the crude product. Flash column chromatography on silica gel in hexane/ethyl acetate (1:1) yields the desired product in the form of a colourless foam.

4"-Methylaminosulfonyloxy-avermectin B$_1$: C$_{49}$H$_{75}$NO$_{16}$S, molecular weight: 965.5. LCMS: t$_{RT}$, B$_{1a}$: 9.88 min., 988.3 (M+Na), 966.6 (M+H), B$_{1b}$: 9.24 min.; NMR (300 MHz, CDCl$_3$) selected data, δH (ppm): 1.48 (s, 3H, CH$_3$-14a), 1.86 (s, 3H, CH$_3$-14a), 2.80 (d, 3H, J=5.5 Hz, H$_3$CNHSO$_2$OC-4"), 3.21 (t, 1H, J=9.2 Hz, CH-4'), 3.28 (m, 1H, CH-2), 3.40 (s, 3H, OCH$_3$), 3.42 (s, 3H, OCH$_3$), 3.95 (d, 1H, J=6.4 Hz, CH-6), 4.08 (t, 1H, J=9.1 Hz, CH-4"), 4.28 (m, 1H, CH-5), 4.67 (m, 2H, CH$_2$-8a), 4.76 (d, 1H, J=2.75 Hz, CH-1'), 4.78 (q, 1H, J=5.5 Hz, HN(CH$_3$)SO$_2$OC-4"), 4.96 (m, 1H, CH-15).

Example P.3

Preparation of 4"-ethylaminosulfonyloxy-avermectin B$_1$

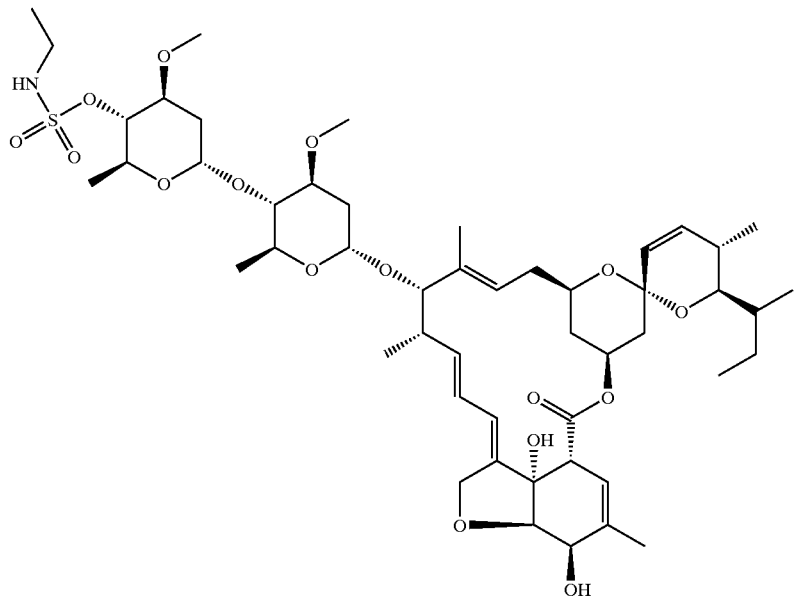

Preparation of N-ethylsulfamoyl chloride (ClSO$_2$NHEt): 16.9 g of ethylamine hydrochloride are added to a solution of 7.3 ml of sulfuryl chloride in 15 ml of acetonitrile. After stirring for 12 hours at the reflux temperature of the mixture, the reaction mass is cooled to room temperature, filtered off and concentrated by evaporation. Vacuum distillation (0.05 mm, 100° C.) of the resulting residue yields the desired product in the form of a colourless oil.

Step A: 240 mg of N-methylsulfamoyl chloride are added at 0° C. to a solution of 400 mg of 5-O-TBDMS-avermectin B$_1$ in 5 ml of dimethylacetamide under argon, and the mixture is left to react at room temperature for 12 hours. The mixture is poured onto saturated NaCl solution, extracted twice with ethyl acetate, dried over Na$_2$SO$_4$ and concentrated by evaporation, yielding the desired intermediate 5-O-TBDMS-4"-O-(N-methyl)-sulfamoyloxy-avermectin B$_1$.

Step B: 0.2 ml of methanesulfonic acid is added at 0° C. to a solution of the crude product obtained in Step A in 1.5 ml of methanol and the mixture is left to react at room temperature for 20 minutes. The reaction mixture is poured onto saturated NaHCO$_3$ solution, concentrated by evaporation, extracted with ethyl acetate, subsequently washed with saturated NaCl solution, dried over Na$_2$SO$_4$ and concentrated by evaporation. Flash column chromatography of the crude product on silica gel in hexane/ethyl acetate (1:1) yields the desired product in the form of a yellow foam.

4"-Ethylaminosulfonyloxy-avermectin B$_1$: C$_{50}$H$_{77}$NO$_{16}$S, molecular weight: 979. LCMS: t$_{RT}$, B$_{1a}$: 10.25 min., 1002.2 (M+Na), 980.5 (M+H), B$_{1b}$: 9.56 min.; NMR (300 MHz, CDCl$_3$) selected data, δH (ppm): 1.21 (t, 3H, J=7.3 Hz, H$_3$CCH$_2$), 1.48 (s, 3H, CH$_3$-14a), 1.86 (s, 3H, CH$_3$-4a), 2.80 (d, 3H, J=5.5 Hz, H$_3$CNHSO$_2$OC-4"), 3.39 (s, 3H, OCH$_3$), 3.42 (s, 3H, OCH$_3$), 3.96 (d, 1H, J=5.9 Hz, CH-6), 4.10 (t, 1H, J=9.1 Hz, CH-4"), 4.28 (m, 1H, CH-5), 4.68 (m, 2H, CH$_2$-8a), 4.73 (t, 1H, J=4.6 Hz, HN(CH$_2$CH$_3$)SO$_2$OC-4"), 4.96 (m, 1H, CH-15).

Example P.4

Preparation of 4"-allylaminosulfonyloxy-avermectin B$_1$

A solution of 238 mg of 4"-sulfamoyloxy-avermectin B1, 138 mg of potassium carbonate and 0.1 ml of allyl bromide in 5 ml of acetonitrile is stirred at room temperature for 5 hours. The solution is poured onto water, extracted with ether and dried over Na$_2$SO$_4$. The desired product is isolated from the crude mixture by column chromatography on silica gel in hexane/ethyl acetate (65:35).

4"-Allylaminosulfonyloxy-avermectin B$_1$: C$_{51}$H$_{77}$NO$_{16}$S, molecular weight: 991.5. LCMS: t$_{RT}$, B$_{1a}$: 9.87 min., 1014.5 (M+Na), 992.5 (M+H), B$_{1b}$: 9.28 min.; NMR (300 MHz, CDCl$_3$) selected data, δH (ppm): 1.48 (s, 3H, CH$_3$-14a), 1.86 (s, 3H, CH$_3$-4a), 3.21 (t, 1H, J=9.2 Hz, CH-4'), 3.29 (m, 1H, CH-2), 3.36 (s, 3H, OCH$_3$), 3.42 (s, 3H, OCH$_3$), 3.96 (d, 1H, J=6.4 Hz, CH-6), 4.13 (t, 1H, J=9.6 Hz, CH-4"), 4.28 (m, 1H, CH-5), 4.67 (m, 2H, CH$_2$-8a), 4.77 (d, 1H, J=2.8 Hz, CH-1'), 4.90 (dd, 1H, J=7.8, 4.6 Hz, HNSO$_2$OC-4"), 4.96 (m, 1H, CH-15), 5.20 (dd, 1H, J=10.5, 1.4 Hz, H$_2$C=CH), 5.28 (dd, 1H, J=16.9, 1.4 Hz, H$_2$C=CH).

Example P.5

Preparation of 4"-diallylaminosulfonyloxy-avermectin B$_1$

A solution of 238 mg of 4"-sulfamoyloxy-avermectin B1, 138 mg of potassium carbonate and 0.1 ml of allyl bromide in 5 ml of acetonitrile is stirred at reflux for 1 hour. The solution is poured onto water, extracted with ether and dried over $Na_2SO_4$. Concentration by evaporation yields the title product.

4"-Diallylaminosulfonyloxy-avermectin $B_1$: $C_{59}H_{81}NO_{16}S$, molecular weight: 1031.5. LCMS: $t_{RT}$, $B_1$a: 11.47 min., 1054.5 (M+Na), 1032.5 (M+H), $B_1$b: 10.89 min.; NMR (300 MHz, $CDCl_3$) selected data, δH (ppm): 1.48 (s, 3H, $CH_3$-14a), 1.86 (s, 3H, $CH_3$-4a), 3.21 (t, 1H, J=9.2 Hz, CH-4'), 3.29 (m, 1H, CH-2), 3.43 (s, 3H, $OCH_3$), 3.48 (s, 3H, $OCH_3$), 3.96 (d, 1H, J=6.4 Hz, CH-6), 4.13 (t, 1H, J=9.1 Hz, CH-4"), 4.28 (m, 1H, CH-5), 4.67 (m, 2H, $CH_2$-8a), 4.75 (m, 1H, CH-1'), 4.96 (m, 1H, CH-15).

Example P.6

4"-(2-Hydroxyethylaminosulfonyloxy)-avermectin $B_1$

A solution of 238 mg of 4"-sulfamoyloxy-avermectin B1, 138 mg of potassium carbonate and 0.1 ml of 2-bromoethanol in 5 ml of acetonitrile is stirred at reflux for 12 hours. The solution is poured onto water, extracted with ether and dried over $Na_2SO_4$. The title product is isolated from the crude mixture by column chromatography on silica gel in hexane/ethyl acetate (30:70).

4"-(2-Hydroxyethylaminosulfonyloxy)-avermectin $B_1$: $C_{50}H77NO_{17}S$, molecular weight: 995.5. LCMS: $t_{RT}$, $B_{1a}$: 8.43 min., 1018.45 (M+Na), 996.5 (M+H), $B_1$b: 7.79 min.; NMR (250 MHz, $CDCl_3$) selected data, δH (ppm): 1.17 (t, 3H, J=6.9 Hz, $H_2$COH), 1.48 (s, 3H, $CH_3$-14a), 1.86 (s, 3H, $CH_3$-4a), 3.21 (t, 1H, J=9.1 Hz, CH-4'), 3.28 (m, 1H, CH-2), 3.31 (m, 2H, $H_2$CNH), 3.41 (s, 3H, $OCH_3$), 3.42 (s, 3H, $OCH_3$), 3.96 (d, 1H, J=6.4 Hz, CH-6), 4.14 (t, 1H, J=9.1 Hz, CH-4"), 4.29 (m, 1H, CH-5), 4.67 (m, 2H, $CH_2$-8a), 4.76 (d, 1H, J=3.2 Hz, CH-1'), 4.96 (m,1H, CH-15), 5.23 (dd,1H, J=6.9, 5.5 Hz, $HNSO_2OC$-4").

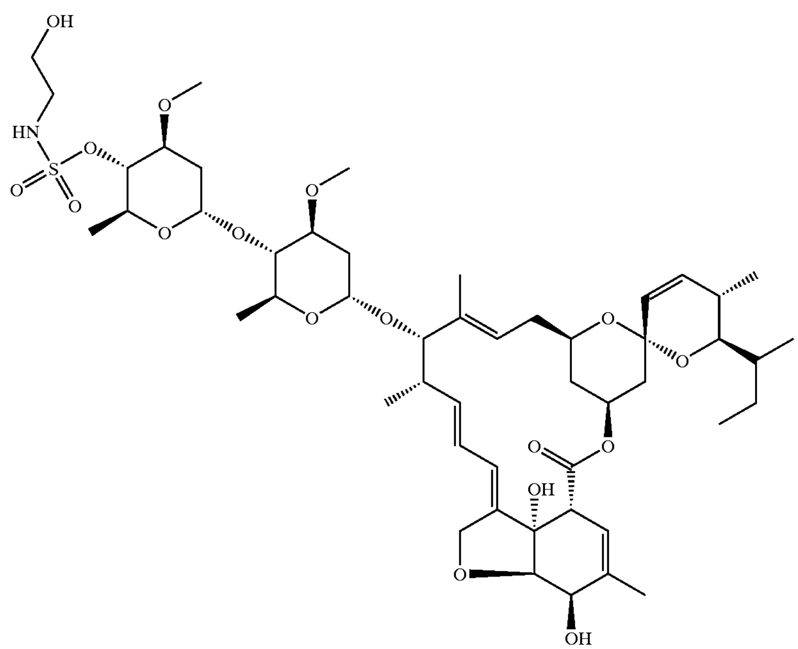

Example P.7

Preparation of 4"-dimethylaminosulfonyloxy-avermectin $B_1$

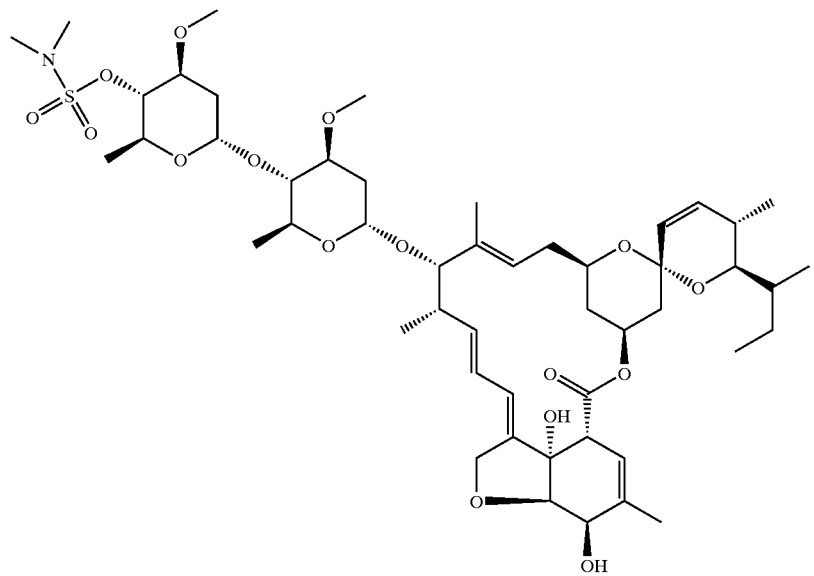

A solution of 238 mg of 4"-sulfamoyloxy-avermectin B1, 138 mg of potassium carbonate and 0.1 ml of iodomethane in 5 ml of acetonitrile is stirred at reflux for 5 hours. The solution is poured onto water, extracted with ether and dried over $Na_2SO_4$. The title product is isolated from the crude mixture by column chromatography on silica gel in hexane/ethyl acetate (1:1).

4"-Dimethylaminosulfonyloxy-avermectin $B_1$: $C_{50}H_{77}NO_{16}S$, molecular weight: 979.5. LCMS: $t_{RT}$, $B_{1a}$: 10.69 min., 1002.5 (M+Na); NMR (300 MHz, $CDCl_3$) selected data, $\delta H$ (ppm): 1.48 (s, 3H, $CH_3$-14a), 1.87 (s, 3H, $CH_3$-4a), 2.91 (s, 6H, $(H_3C)_2N$), 3.21 (t, 1H, J=9.1 Hz, CH-4'), 3.28 (m, 1H, CH-2), 3.40 (s, 3H, $OCH_3$), 3.43 (s, 3H, $OCH_3$), 3.96 (d, 1H, J=6.4 Hz, CH-6), 4.08 (t, 1H, J=9.1 Hz, HC-4"), 4.68 (m, 2H, $CH_2$-8a), 4.76 (bd, 1H, J=2.8 Hz, CH-1'), 4.96 (m,1H, CH-15).

Example P.8

Preparation of 4"-dipropargylaminosulfonyloxy-avermectin $B_1$

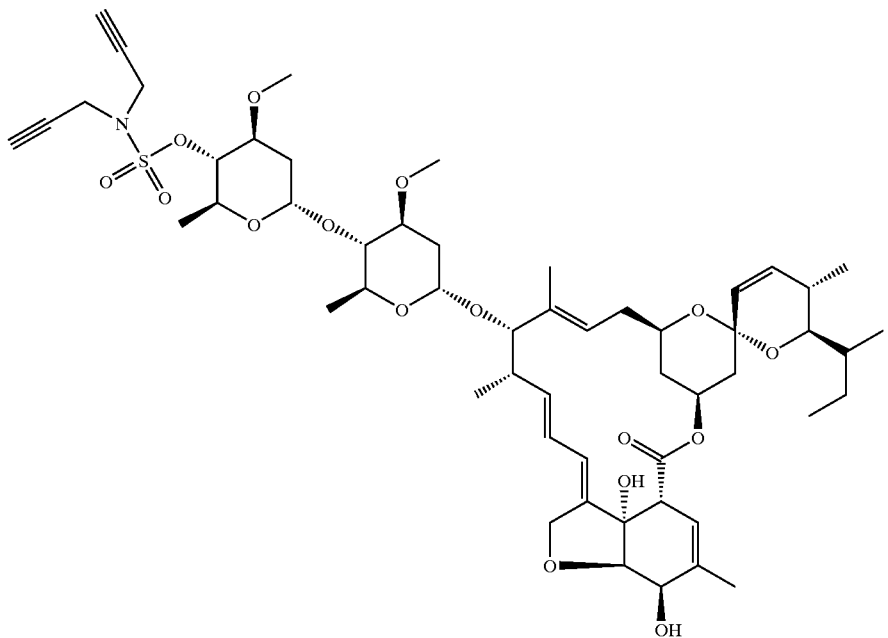

A solution of 238 mg of 4"-sulfamoyloxy-avermectin B1, 138 mg of potassium carbonate and 0.14 ml of propargyl bromide (80% in toluene) in 5 ml of acetonitrile is stirred at room temperature for 18 hours. The solution is poured onto water, extracted with ether and dried over $Na_2SO_4$. The desired product is isolated from the crude mixture by column chromatography on silica gel in hexane/ethyl acetate (65:35).

4"-Dipropargylaminosulfonyloxy-avermectin $B_1$: $C_{54}H77NO_{16}S$, molecular weight: 1027.5. LCMS: $t_{RT}$, $B_{1a}$: 10.62 min., 1050.4 (M+Na), 1028.5 (M+H), $B_1$b: 9.98 min.; NMR (250 MHz, $CDCl_3$) selected data, δH (ppm): 1.48 (s, 3H, $CH_3$-14a), 1.86 (s, 3H, $CH_3$-4a), 2.34 (t, 2H, J=2.3 Hz, $HCCCH_2$), 3.20 (t, 1H, J=8.7 Hz, CH-4'), 3.28 (m, 1H, CH-2), 3.40 (s, 3H, $OCH_3$), 3.42 (s, 3H, $OCH_3$), 3.96 (d, 1H, J=5.9 Hz, CH-6), 4.23 (ABX System, 4H, J=17.8, 2.9 Hz, $H_2CNHSO_2OC$-4"), 4.67 (m, 2H, $CH_2$-8a), 4.76 (bd, 1H, J=3.2 Hz, CH-1'), 4.96 (m, 1H, CH-15).

Example P.9

Preparation of 4"-bis(cyanomethyl) aminosulfonyloxy-avermectin $B_1$

A solution of 238 mg of 4"-sulfamoyloxy-avermectin B1, 138 mg of potassium carbonate and 0.09 ml of bromoacetonitrile in 5 ml of acetonitrile is stirred at room temperature for 10 hours. The solution is poured onto water, extracted with ether and dried over $Na_2SO_4$. The desired product is isolated from the crude mixture by column chromatography on silica gel in hexane/ethyl acetate (60:40).

4"-Dicyanomethylaminosulfonyloxy-avermectin $B_1$: $C_{52}H_{75}N_3O_{16}S$, molecular weight: 1029.5. LCMS: $t_{RT}$, $B_{1a}$: 9.88 min., 1052.4 (M+Na), 1030.5 (M+H), $B_{1b}$: 9.29 min.; NMR (250 MHz, $CDCl_3$) selected data, δH (ppm): 1.48 (s, 3H, $CH_3$-14a), 1.86 (s, 3H, $CH_3$-4a), 3.19 (t, 1H, J=8.7 Hz, CH-4'), 3.28 (m, 1H, CH-2), 3.40 (s, 3H, $OCH_3$), 3.42 (s, 3H, $OCH_3$), 3.96 (d, 1H, J=6.4 Hz, CH-6), 4.22 (t, 1H, J=9.1 Hz, CH-4"), 4.38 (AB system, 4H, J=18.3 Hz, $H_2CCN$), 4.67 (m, 2H, $CH_2$-8a), 4.76 (bd, 1H, J=3.2 Hz, CH-1'), 4.96 (m, 1H, CH-15).

Example P.10

Preparation of 4"-pyrrolidinosulfonyloxy-avermectin $B_1$

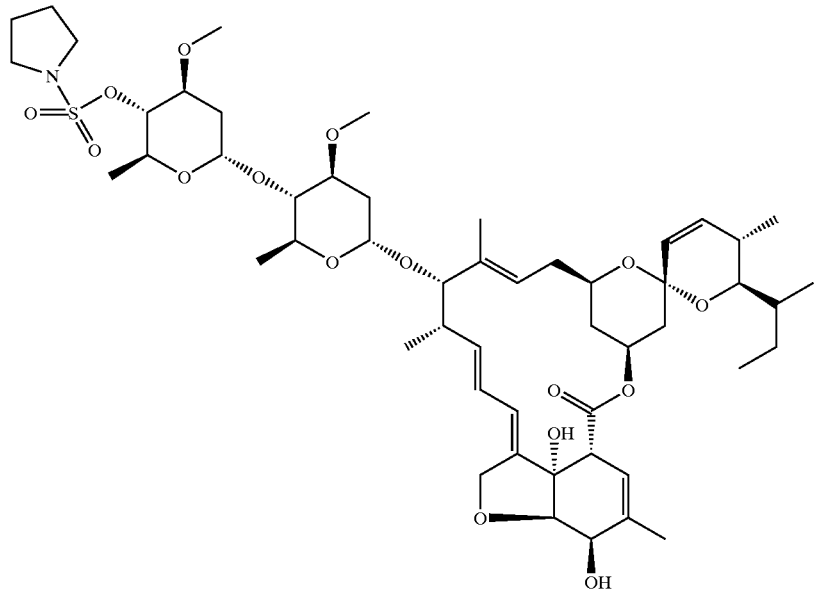

A solution of 238 mg of 4"-sulfamoyloxy-avermectin B1, 138 mg of potassium carbonate and 0.15 ml of 1,4-dibromobutane in 5 ml of acetonitrile is stirred at reflux for 12 hours. The solution is poured onto water, extracted with ether and dried over $Na_2SO_4$. The desired product is isolated from the crude mixture by column chromatography on silica gel in hexane/ethyl acetate (60:40).

4"-Pyrrolidinosulfonyloxy-avermectin $B_1$: $C_{52}H_{79}NO_{16}S$, molecular weight: 1005.5. LCMS: $t_{RT}$, $B_1a$: 10.67 min., 1028.5 (M+Na), 1006.5 (M+H), $B_{1b}$: 10.03 min.; NMR (250 MHz, $CDCl_3$) selected data, δH (ppm): 1.48 (s, 3H, $CH_3$-14a), 1.86 (s, 3H, $CH_3$-4a), 3.21 (t, 1H, J=8.7 Hz, CH-4'), 3.28 (m, 1H, CH-2), 3.38 (s, 3H, $OCH_3$), 3.42 (s, 3H, $OCH_3$), 3.96 (d, 1H, J=5.9 Hz, CH-6), 4.28 (m, 1H, HC-5), 4.67 (m, 2H, $CH_2$-8a), 4.76 (bd, 1H, J=3.2 Hz, CH-1'), 4.96 (m,1H, CH-15).

Example P.11

Preparation of 4"-benzoylaminosulfonyloxy-avermectin $B_1$

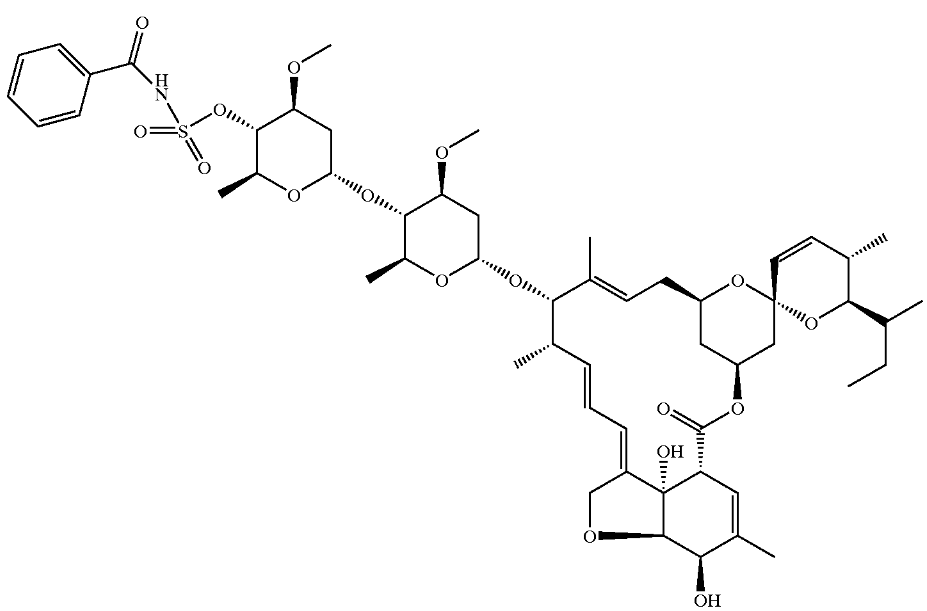

A mixture of 200 mg of 4"-sulfamoyloxy-avermectin $B_1$, 0.15 ml of benzoyl chloride in 3 ml of ethyl acetate and 3 ml of saturated aqueous $NaHCO_3$ solution is stirred at 70° C. for 6 hours. The mixture is poured onto water, extracted with ether and dried over $Na_2SO_4$. The desired product is isolated from the crude mixture by column chromatography on silica gel in hexane/ethyl acetate (1:1).

4"-Benzoylaminosulfonyloxy-avermectin $B_1$: $C_{55}H_{77}NO_{17}S$, molecular weight: 1055.5. LCMS: $t_{RT}$, $B_{1a}$: 9.83 min., 1078.4 (M+Na), 1056.5 (M+H), B1b: 9.18 min.

Example P.12

Preparation of 4"-epi-sulfamoyloxy-avermectin B1 of the formula:

50 mg of sulfamoyl chloride are added at 0° C. to a solution of 197 mg of 4"-epi-5-O-TBDMS-avermectin $B_1$ (0.2 mmol) in 3 ml of dimethylacetamide under argon, and the mixture is left to react at room temperature for 3 hours. The mixture is poured onto cold-saturated NaCl solution, extracted twice with ethyl acetate, dried over $Na_2SO_4$ and concentrated by evaporation, yielding 5-O-TBDMS-4"-epi-sulfamoyloxy-avermectin $B_1$.

1 ml of HF-pyridine reagent (25 g of 70% HF-pyridine solution, 27.5 ml of tetrahydrofuran, 12.5 ml of pyridine) is added to a solution of 5-O-TBDMS-4"-epi-sulfamoyloxy-avermectin $B_1$ in 5 ml of absolute tetrahydrofuran and the mixture is left to stand at room temperature for 12 hours. The reaction mixture is poured onto water and extracted twice with ether. Washing with saturated $NaHCO_3$ solution, drying over $Na_2SO_4$ and concentration by evaporation yield the crude product. Flash column chromatography on silica gel in hexane/ethyl acetate (1:1) yields the desired product.

4"-epi-Sulfamoyloxy-avermectin $B_1$: $C_{48}H_{73}NO_{16}S$, molecular weight: 951.5. LCMS: $t_{RT}$, $B_{1a}$: 9.13 min., 974.5 (M+Na), 952.5 (M+H), $B_{1b}$: 8.49 min.

The compounds listed in Table A and in Tables 1 to 6 can also be prepared analogously to the above Preparation Examples.

TABLE A
Compounds of formula:
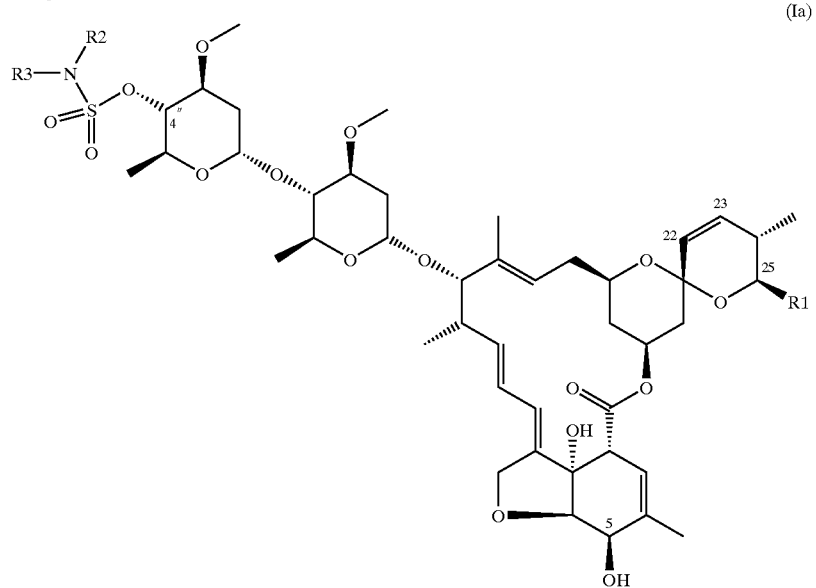
(Ia)
or of formula
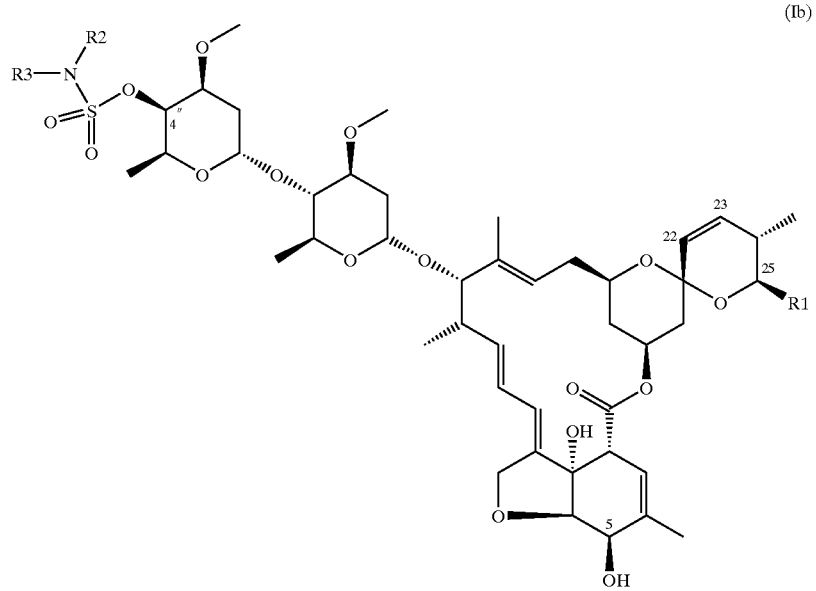
(Ib)
wherein $R_1$ is sec-butyl (B1a) or isopropyl (B1b) and $R_2$ is hydrogen:
| No. | formula | $R_2$ | $R_3$ | retention time (min.) $B_{1a}$ | $B_{1b}$ |
|---|---|---|---|---|---|
| P.1 | Ia | H | H | 9.08 | 8.44 |
| P.2 | Ia | H | $CH_3$ | 9.88 | 9.24 |
| P.3 | Ia | H | $CH_2CH_3$ | 10.25 | 9.56 |
| P.4 | Ia | H | allyl | 9.47 | 9.28 |
| P.5 | Ia | allyl | allyl | 11.47 | 10.89 |
| P.6 | Ia | H | $CH_2CH_2OH$ | 8.43 | 7.77 |
| P.7 | Ia | $CH_3$ | $CH_3$ | 10.69 | |
| P.8 | Ia | propargyl | propargyl | 10.62 | 9.98 |
| P.9 | Ia | $CH_2CN$ | $CH_2CN$ | 9.88 | 9.29 |
| P.10 | Ia | —$CH_2CH_2CH_2CH_2$— | | 10.67 | 10.03 |
| P.11 | Ia | H | C(O)Ph | 9.83 | 9.18 |
| P.12 | Ib | H | H | 9.13 | 8.49 |
| P.13 | Ia | H | C(O)isoPr | 9.65 | 8.98 |
| P.14 | Ia | H | C(O)Me | 9.12 | 8.43 |

TABLE A-continued
Compounds of formula:
(Ia)
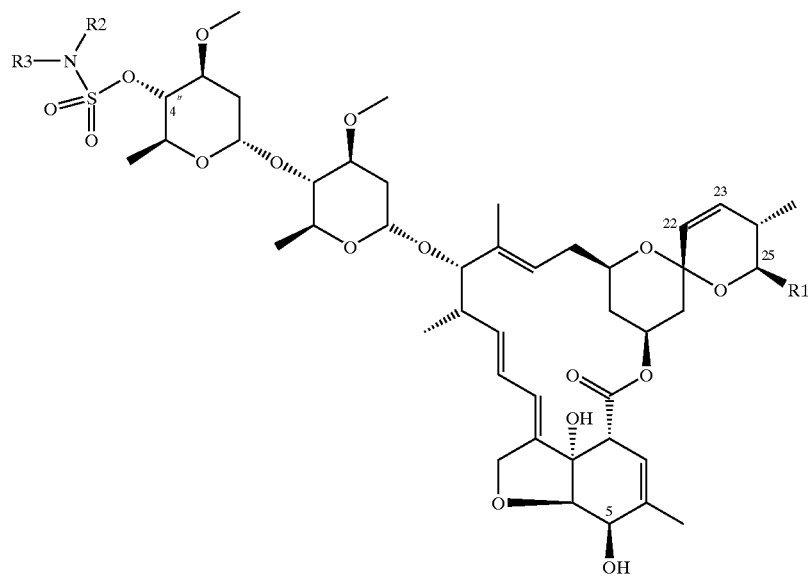
or of formula
(Ib)
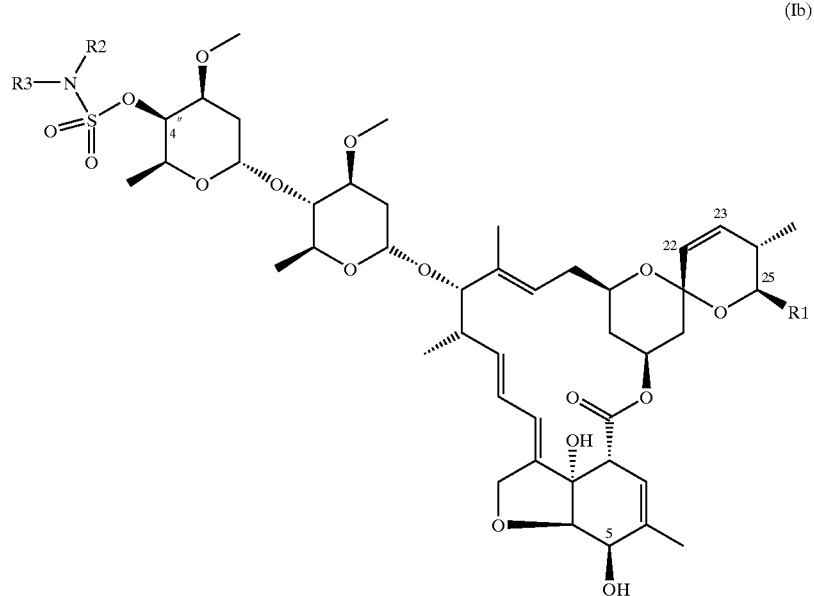
wherein $R_1$ is sec-butyl (B1a) or isopropyl (B1b) and $R_2$ is hydrogen:
| No. | formula | $R_2$ | $R_3$ | retention time (min.) $B_{1a}$ | $B_{1b}$ |
|---|---|---|---|---|---|
| P.15 | Ia | H | C(O)Et | 9.28 | 8.54 |
| P.16 | Ia | H | C(O)cyclopropyl | 9.44 | 8.80 |
| P.17 | Ia | H | C(O)OCH$_3$ | 9.55 | 8.91 |

TABLE B

Compounds of formula (I):

| No. | R₂ | retention time (min.) B1a | B1b |
|---|---|---|---|
| B.1 | isopropyl | | |
| B.2 | propyl | | |
| B.3 | n-butyl | | |
| B.4 | sec-butyl | | |
| B.5 | isobutyl | | |
| B.6 | tert-butyl | | |
| B.7 | CH(CH₃)CH(CH₃)₂ | | |
| B.8 | CH(CH₂CH₃)CH₂Cl | | |
| B.9 | CH(CH₃)CH₂OCH₃ | | |
| B.10 | 2-chloro-propyl | | |
| B.11 | 3-chloro-propyl | | |
| B.12 | 2-chloro-ethyl | | |
| B.13 | CH₂CH₂OCH₃ | | |
| B.14 | 2-fluoro-ethyl | | |
| B.15 | 2-morpholino-ethyl | | |
| B.16 | 2-pyrrolidino-ethyl | | |
| B.17 | cyclopropyl | | |
| B.18 | cyclobulyl | | |
| B.19 | cyclopentyl | | |
| B.20 | cyclohexyl | | |
| B.21 | bis(trifluoromethyl)methyl | | |
| B.22 | benzyl | | |
| B.23 | 2-methylallyl | | |
| B.24 | 3-methylallyl | | |
| B.25 | CH₂C(O)OCH₃ | | |
| B.26 | CH₂CH₂C(O)OCH₃ | | |
| B.27 | 2-phthalimido-ethyl | | |
| B.28 | 2-aminoethyl | | |
| B.29 | 2-methylaminoethyl | | |
| B.30 | 2-dimethylaminoethyl | | |
| B.31 | CH₂CH₂OC₂H₅ | | |
| B.32 | CH₂CH₂OCH₂CH₂OCH₃ | | |
| B.33 | 3-phthalimido-propyl | | |
| B.34 | 4-phthalimido-butyl | | |
| B.35 | CH₂CONH₂ | | |
| B.36 | CH₂COOH | | |
| B.37 | (2-fluorophenyl)methyl | | |
| B.38 | (3-fluorophenyl)methyl | | |
| B.39 | (2,6-difluorophenyl)methyl | | |
| B.40 | (4-fluorophenyl)methyl | | |
| B.41 | (4-trifluoromethylphenyl)methyl | | |

B.42 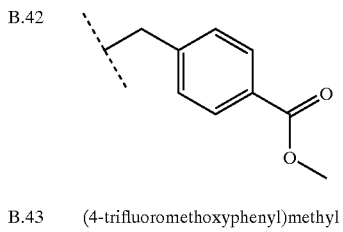

| B.43 | (4-trifluoromethoxyphenyl)methyl | | |
|---|---|---|---|
| B.44 | (4-difluoromethylphenyl)methyl | | |

B.45 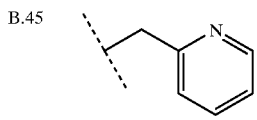

B.46 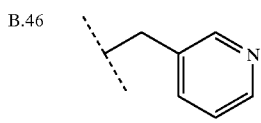

B.47 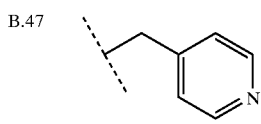

TABLE B-continued

Compounds of formula (I):

| No. | R₂ | retention time (min.) B1a | B1b |
|---|---|---|---|

B.48 (isoxazole structure)

B.49 (4-cyanobenzyl structure)

| B.50 | (4-methoxyphenyl)methyl | | |

TABLE 1

A compound of formula (Ia) wherein R₁ is sec-butyl (B1a) or isopropyl (B1b), R₃ hydrogen and R₂ corresponds to one of the readicals of Table B listed under B.1 to B.50.

TABLE 2

A compound of formula (Ib) wherein R₁ is sec-butyl (B1a) or isopropyl (B1b), R₃ hydrogen and R₂ corresponds to one of the radicals of Table B listed under B.1 to B.50.

TABLE C

Compounds of formula (I)

| No. | R₄ | retention time (min.) B1a | B1b |
|---|---|---|---|
| C.001 | isopropyl | | |
| C.002 | propyl | | |
| C.003 | n-butyl | | |
| C.004 | sec-butyl | | |
| C.005 | isobutyl | | |
| C.006 | tert-butyl | | |
| C.007 | methyl | | |
| C.008 | ethyl | | |
| C.009 | vinyl | | |
| C.010 | 2-chloro-propyl | | |
| C.011 | 3-chloro-propyl | | |
| C.012 | 2-chloro-ethyl | | |
| C.013 | CH₂CH₂OCH₃ | | |
| C.014 | allyl | | |
| C.015 | CH₂OCH₃ | | |
| C.016 | CH₂Ophenyl | | |
| C.017 | cyclopropyl | | |
| C.018 | cyclopentyl | | |
| C.019 | cyclohexyl | | |
| C.020 | CH₂CH₂NH₂ | | |
| C.021 | benzyl | | |
| C.022 | fluoromethyl | | |
| C.023 | difluoromethyl | | |

TABLE C-continued

Compounds of formula (I)

| No. | R₄ | retention time (min.) B1a | B1b |
|---|---|---|---|
| C.024 | 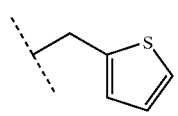 | | |
| C.025 | 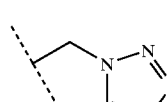 | | |
| C.026 | CH₂OCH₂CH₂Ome | | |
| C.027 | OCH₃ | | |
| C.028 | OCH₂CH₃ | | |
| C.029 | O-allyl | | |
| C.030 | OCH₂CH₂OH | | |
| C.031 | NH₂ | | |
| C.032 | NHCH₃ | | |
| C.033 | N(CH₃) | | |
| C.034 | benzyl | | |

TABLE 3

A compound of formula (Ia) wherein $R_1$ is sec-butyl (B1a) or isopropyl (B1b), $R_2$ is C(=O)$R_4$ and $R_3$ hydrogen, and $R_2$ corresponds to one of the radicals of Table C listed under C.1 to C.034.

TABLE 4

A compound of formula (Ib) wherein $R_1$ is sec-butyl (B1a) or isopropyl (B1b), $R_2$ is C(=O)$R_4$ and $R_3$ hydrogen, and $R_2$ corresponds to one of the radicals of Table C listed under C.1 to C.034.

TABLE D

Compounds of formula (I)

| No. | R₂ | R₃ | retention time (min.) B1a | B1b |
|---|---|---|---|---|
| D.001 | —CH₂CH₂— | | | |
| D.002 | —CH₂CH₂CH₂— | | | |
| D.003 | —CH₂(CH₂)₃CH₂— | | | |
| D.004 | —CH₂CH₂OCH₂CH₂— | | | |
| D.005 | ethyl | ethyl | | |
| D.006 | ethyl | methyl | | |
| D.007 | allyl | methyl | | |
| D.008 | CH₂CH₂OH | methyl | | |
| D.009 | C(O)CH₃ | methyl | | |
| D.010 | C(O)OCH₃ | methyl | | |
| D.011 | C(O)Ph | methyl | | |
| D.012 | SO₂NH₂ | H | | |
| D.013 | SO₂NMe₂ | H | | |
| D.014 | =N⁺=N⁻ | | | |
| D.015 | benzyl | benzyl | | |
| D.016 | (4-CF₃O-phenyl)methyl | (4-CF₃O-phenyl)methyl | | |
| D.017 | (4-methoxyphenyl)methyl | (4-methoxyphenyl)methyl | | |

TABLE 5

A compound of formula (Ia) wherein $R_1$ is sec-butyl (B1a) or isopropyl (B1b), $R_2$ and $R_3$ correspond to one of the radicals of Table D listed under D.1 to D.016.

TABLE 6

A compound of formula (Ib) wherein $R_1$ is sec-butyl (B1a) or isopropyl (B1b), $R_2$ and $R_3$ correspond to one of the radicals of Table D listed under D.1 to D.016.

Formulation Examples for use in crop protection (%=percent by weight)

Example F1

| Emulsifiable concentrates | a) | b) | c) |
| --- | --- | --- | --- |
| active ingredient | 25% | 40% | 50% |
| calcium dodecylbenzenesulfonate | 5% | 8% | 6% |
| castor oil polyethylene glycol ether (36 mol EO) | 5% | — | — |
| tributylphenol polyethylene glycol ether (30 mol EO) | — | 12% | 4% |
| cyclohexanone | — | 15% | 20% |
| xylene mixture | 65% | 25% | 20% |

Mixing finely ground active ingredient and additives gives an emulsifiable concentrate which yields emulsions of the desired concentration on dilution with water.

Example F2

| Solutions | a) | b) | c) | d) |
| --- | --- | --- | --- | --- |
| active ingredient | 80% | 10% | 5% | 95% |
| ethylene glycol monomethyl ether | — | 20% | — | — |
| polyethylene glycol (MW 400) | — | — | 70% | — |
| N-methylpyrrolid-2-one | 20% | — | — | — |
| epoxidised coconut oil | — | — | — | 1% |
| benzine (boiling range: 160–190°) | — | — | 94% | — |

Mixing finely ground active ingredient and additives gives a solution suitable for use in the form of microdrops.

Example F3

| Granules | a) | b) | c) | d) |
| --- | --- | --- | --- | --- |
| active ingredient | 5% | 10% | 8% | 21% |
| kaolin | 94% | — | 79% | 54% |
| highly dispersed silicic acid | 1% | — | 13% | 7% |
| attapulgite | — | 90% | — | 18% |

The active ingredient is dissolved in dichloromethane, the solution is sprayed onto the carrier mixture and the solvent is evaporated off in vacuo.

Example F4

| Wettable powders | a) | b) | c) |
| --- | --- | --- | --- |
| active ingredient | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| octylphenol polyethylene glycol ether (7–8 mol EO) | — | 2% | — |
| highly dispersed silicic acid | 5% | 10% | 10% |
| kaolin | 62% | 27% | — |

Active ingredient and additives are mixed together and the mixture is ground in a suitable mill, yielding wettable powders that can be diluted with water to form suspensions of the desired concentration.

Example F5

| Emulsifiable concentrate | |
| --- | --- |
| active ingredient | 10% |
| octylphenol polyethylene glycol ether (4–5 mol EO) | 3% |
| calcium dodecylbenzenesulfonate | 3% |
| castor oil polyethylene glycol ether (36 mol EO) | 4% |
| cyclohexanone | 30% |
| xylene mixture | 50% |

Mixing finely ground active ingredient and additives gives an emulsifiable concentrate which yields emulsions of the desired concentration on dilution with water.

Example F6

| Extruder granules | |
| --- | --- |
| active ingredient | 10% |
| sodium lignosulfonate | 2% |
| carboxymethylcellulose | 1% |
| kaolin | 87% |

Active ingredient and additives are mixed together, the mixture is ground, moistened with water, extruded and granulated and the granules are dried in a stream of air.

Example F7

| Coated granules | |
| --- | --- |
| active ingredient | 3% |
| polyethylene glycol (MW 200) | 3% |
| kaolin | 94% |

Uniform application of the finely ground active ingredient to the kaolin moistened with polyethylene glycol in a mixer yields non-dusty coated granules.

Example F8

| Suspension concentrate | |
| --- | --- |
| active ingredient | 40% |
| ethylene glycol | 10% |
| nonylphenol polyethylene glycol ether (15 mol EO) | 6% |
| sodium lignosulfonate | 10% |
| carboxymethylcellulose | 1% |
| aqueous formaldehyde solution (37%) | 0.2% |
| aqueous silicone oil emulsion (75%) | 0.8% |
| water | 32% |

Mixing finely ground active ingredient and additives gives a suspension concentrate which yields suspensions of the desired concentration on dilution with water.

BIOLOGICAL EXAMPLES

Example B1

Action Against *Spodoptera littoralis*

Young soybean plants are sprayed with an aqueous emulsion spray mixture comprising 12.5 ppm of test compound and, after the spray-coating has dried, the plants are populated with 10 caterpillars of *Spodoptera littoralis* in the first stage and then placed in a plastics container. 3 days later, the percentage reduction in population and the percentage reduction in feeding damage (% activity) are determined by comparing the number of dead caterpillars and the feeding damage on the treated plants with that on untreated plants.

Compounds P.1 to P.11 and of Tables 1 to 3 exhibit good activity in this test. In particular, compounds P.1 and P.2 are more than 80% effective.

Example B2

Action gainst *Spodoptera littoralis*, Systemic

Maize seedlings are placed in the test solution. 6 days later, the leaves are cut off, placed on moist filter paper in a petri dish and infested with 12 to 15 *Spodoptera littoralis* larvae in the $L_1$ stage. 4 days later, the percentage reduction in population (% activity) is determined by comparing the number of dead caterpillars on treated plants with that on untreated plants.

Compounds P.1 to P.11 and of Tables 1 to 3 exhibit good activity in this test. In particular, P.1 and P.2 are more than 80% effective.

Example B3

Action Against *Heliothis Virescens*

30-35 eggs of *Heliothis virescens*, from 0 to 24 hours old, are placed on filter paper in a petri dish on a layer of artificial nutrient. 0.8 ml of the test solution is then pipetted onto the filter paper. Evaluation is made 6 days later. The percentage reduction in population (% activity) is determined by comparing the number of dead eggs and larvae on treated plants with that on untreated plants.

Compounds P.1 to P.11 and of Tables 1 to 3 exhibit good activity in this test. In particular, compounds P.1, P.2, P.3 and P.7 are more than 80% effective.

Example B4

Action Against *Plutella xylostella* Caterpillars

Young cabbage plants are sprayed with an aqueous emulsion spray mixture comprising 12.5 ppm of test compound. After the spray-coating has dried, the cabbage plants are populated with 10 caterpillars of *Plutella xylostella* in the first stage and placed in a plastics container. Evaluation is made 3 days later. The percentage reduction in population and the percentage reduction in feeding damage (% activity) are determined by comparing the number of dead caterpillars and the feeding damage on the treated plants with that on the untreated plants.

Compounds P.1 to P.11 and of Tables 1 to 3 exhibit good activity in this test. In particular, compounds P.1, P.2, P.3 and P.7 are more than 80% effective.

Example B5

Action Against *Diabrotica balteata*

Maize seedlings are sprayed with an aqueous emulsion spray mixture comprising 12.5 ppm of the test compound and, after the spray-coating has dried, the maize seedlings are populated with 10 *Diabrotica balteata* larvae in the second stage and then placed in a plastics container. 6 days later, the percentage reduction in population (% activity) is determined by comparing the number of dead larvae on the treated plants with that on untreated plants.

Compounds P.1 to P.11 and of Tables 1 to 3 exhibit good activity in this test. In particular, compounds P.1, P.2, P.3 and P.7 are more than 80% effective.

Example B6

Action Against *Tetranychus urticae*

Young bean plants are populated with a mixed population of *Tetranychus urticae* and sprayed one day later with an aqueous emulsion spray mixture comprising 12.5 ppm of test compound. The plants are incubated for 6 days at 25° C. and subsequently evaluated. The percentage reduction in population (% activity) is determined by comparing the number of dead eggs, larvae and adults on the treated plants with that on untreated plants.

Compounds P.1 to P.11 and of Tables 1 to 3 exhibit good activity in this test. In particular, compounds P.1, P.2, P.3 and P.7 are more than 80% effective.

What is claimed is:

1. A compound of formula:

-continued

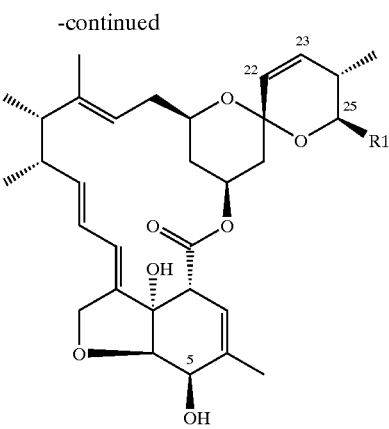

wherein the bond marked by ~~~ indicates the S- as well as the R-isomer at the 4''-position; and wherein $R_1$ is $C_1$–$C_{12}$alkyl, $C_3$–$C_8$cycloalkyl; or $C_2$–$C_{12}$alkenyl;

$R_2$ is hydrogen, unsubstituted or mono- to penta-substituted $C_1$–$C_{12}$alkyl or unsubstituted or mono- to penta-substituted $C_2$–$C_{12}$alkenyl; unsubstituted or mono- to penta-substituted $C_2$–$C_{12}$alkynyl; —C(O)$R_4$ or $SO_2R_4$;

$R_3$ is hydrogen, $C_1$–$C_{12}$alkyl, mono- to penta-substituted $C_1$–$C_{12}$alkyl, unsubstituted or mono- to penta-substituted $C_3$–$C_{12}$cycloalkyl, unsubstituted or mono- to penta-substituted $C_2$–$C_{12}$alkenyl; or unsubstituted or mono- to penta-substituted $C_2$–$C_{12}$alkynyl; or $R_2$ and $R_3$ together are a three- to seven-membered alkylene bridge or a four- to seven-membered alkenylene bridge wherein one $CH_2$ group in the alkylene or alkenylene may have been replaced by O, S or $NR_5$; or are a group =$N^+$=$N^-$, and wherein the substituents of the alkyl, alkenyl, alkynyl, alkylene, alkenylene and cycloalkyl radicals defined under $R_2$ and $R_3$ are selected from the group consisting of OH, halogen, halo-$C_1$–$C_2$alkyl, CN, $NO_2$, $C_2$–$C_6$alkynyl; $C_3$–$C_8$cycloalkyl unsubstituted or substituted by from one to three methyl groups, norbornylenyl; $C_3$–$C_8$cycloalkenyl unsubstituted or substituted by from one to three methyl groups; $C_3$–$C_8$halocycloalkyl, $C_1$–$C_{12}$alkoxy, $C_1$–$C_6$alkoxy-$C_1$–$C_6$alkyl, $C_1$–$C_6$alkoxy-$C_1$–$C_6$alkoxy-$C_1$–$C_6$alkyl, $C_3$–$C_8$cycloalkoxy, $C_1$–$C_{12}$haloalkoxy, $C_1$–$C_{12}$alkylthio, $C_3$–$C_8$cycloalkylthio, $C_1$–$C_{12}$haloalkylthio, $C_1$–$C_{12}$alkylsulfinyl, $C_3$–$C_8$cycloalkylsulfinyl, $C_1$–$C_{12}$haloalkylsulfinyl, $C_3$–$C_8$halocycloalkylsulfinyl, $C_1$–$C_{12}$alkylsulfonyl, $C_3$–$C_8$cycloalkylsulfonyl, $C_1$–$C_{12}$haloalkylsulfonyl, $C_3$–$C_8$halocycloalkylsulfonyl, $C_2$–$C_8$alkenyl, $C_2$–$C_8$alkynyl, NH($C_1$–$C_6$alkyl), N($C_1$–$C_6$alkyl)$_2$, —C(=O)$R_4$, —NHC(=O)$R_7$, —P(=O) $(OC_1$–$C_6$alkyl)$_2$; aryl, heterocyclyl, aryloxy, heterocyclyloxy; aryl, heterocyclyl, aryloxy, heterocyclyloxy that, depending upon the possibilities of substitution at the ring, are mono- to penta-substituted by substituents selected from the group consisting of OH, halogen, CN, $NO_2$, $C_1$–$C_{12}$alkyl, $C_3$–$C_8$cycloalkyl, $C_1$–$C_{12}$haloalkyl, $C_1$–$C_{12}$alkoxy, $C_1$–$C_{12}$haloalkoxy, $C_1$–$C_{12}$alkylthio, $C_1$–$C_{12}$haloalkylthio, $C_1$–$C_6$alkoxy-$C_1$–$C_6$alkyl, dimethylamino-$C_1$–$C_6$alkoxy, $C_2$–$C_8$alkenyl, $C_2$–$C_8$alkynyl, phenoxy, phenyl-$C_1$–$C_6$alkyl; phenoxy unsubstituted or substituted by from one to three substituents selected independently of one another from halogen, methoxy, trifluoromethyl and trifluoromethoxy; phenyl-$C_1$–$C_6$alkoxy unsubstituted or substituted in the aromatic ring by from one to three substituents selected independently of one another from halogen, methoxy, trifluoromethyl and trifluoromethoxy; phenyl-$C_2$–$C_6$alkenyl, phenyl-$C_2$–$C_6$alkynyl, methylenedioxy, —C(=O)$R_4$, —O—C(=O)$R_7$, —NH—C(=O)$R_7$, $NH_2$, NH($C_1$–$C_{12}$alkyl), N($C_1$–$C_{12}$alkyl)$_2$, $C_1$–$C_6$alkylsulfinyl, $C_3$–$C_8$cycloalkylsulfinyl, $C_1$–$C_6$haloalkylsulfinyl, $C_3$–$C_8$halocycloalkylsulfinyl, $C_1$–$C_6$alkylsulfonyl, $C_3$–$C_8$cycloalkylsulfonyl, $C_1$–$C_6$haloalkylsulfonyl and $C_3$–$C_8$halocycloalkylsulfonyl;

$R_4$ is H, OH, $C_1$–$C_8$alkyl, $C_1$–$C_8$alkyl mono- to hepta-substituted by halogen, nitro, $C_1$–$C_8$alkoxy, OH, SH, $NH_2$, NH($C_1$–$C_{12}$alkyl) or N($C_1$–$C_{12}$alkyl)$_2$; $C_1$–$C_8$alkoxy, halo-$C_1$–$C_8$alkoxy, $C_3$–$C_8$cycloalkyl, $C_3$–$C_8$cycloalkoxy, $C_2$–$C_8$alkenyl, $C_2$–$C_8$alkenyloxy, $C_2$–$C_8$alkynyl, $C_2$–$C_8$alkynyloxy, $NH_2$, NH($C_1$–$C_{12}$alkyl), N($C_1$–$C_{12}$alkyl)$_2$, aryl, aryloxy, benzyl, benzyloxy, heterocyclyl, heterocyclyloxy, heterocyclylmethyl or heterocyclylmethoxy; wherein the radicals aryl, aryloxy, benzyl, benzyloxy, heterocyclyl, heterocyclyloxy, heterocyclylmethyl and heterocyclylmethoxy are unsubstituted or, depending upon the possibilities of substitution at the ring, are substituted by from one to three substituents selected independently of one another from halogen, $C_1$–$C_{12}$alkyl, $C_1$–$C_{12}$haloalkyl, $C_1$–$C_{12}$alkoxy, $C_1$–$C_{12}$haloalkoxy, $C_1$–$C_6$alkoxy-$C_1$–$C_6$alkoxy, $C_1$–$C_{12}$alkylthio, $C_1$–$C_{12}$haloalkylthio, $C_2$–$C_8$alkenyloxy, $C_2$–$C_8$alkynyloxy, nitro and cyano;

$R_5$ is $C_1$–$C_8$alkyl, $C_3$–$C_8$cycloalkyl, $C_2$–$C_8$alkenyl, $C_2$–$C_8$alkynyl, benzyl or —C(=O)—$R_6$;

$R_6$ is H, OH, SH, $NH_2$, NH($C_1$–$C_{12}$alkyl), N($C_1$–$C_{12}$alkyl)$_2$, $C_1$–$C_{12}$alkyl, $C_1$–$C_{12}$haloalkyl, $C_1$–$C_{12}$alkoxy, $C_1$–$C_{12}$haloalkoxy, $C_1$–$C_6$alkoxy-$C_1$–$C_6$alkoxy, $C_1$–$C_{12}$alkylthio, $C_2$–$C_8$alkenyloxy, $C_2$–$C_8$alkynyloxy; phenyl, phenoxy, benzyloxy, NH-phenyl, N($C_1$–$C_6$alkyl)-phenyl, NH—$C_1$–$C_6$alkyl-C(=O)—$R_8$, N($C_1$–$C_6$alkyl)-$C_1$–$C_6$alkyl-C(=O)—$R_8$; or phenyl, phenoxy, benzyloxy, NH-phenyl or N($C_1$–$C_6$alkyl)-phenyl each of which is substituted in the aromatic ring by from one to three substituents selected independently of one another from halogen, $C_1$–$C_6$alkoxy, $C_1$–$C_6$haloalkyl and $C_1$–$C_6$haloalkoxy;

$R_7$ is H, $C_1$–$C_{12}$alkyl, $C_1$–$C_{12}$haloalkyl, $C_2$–$C_8$alkenyl, $C_2$–$C_8$alkynyl, phenyl, benzyl, $NH_2$, NH($C_1$–$C_{12}$alkyl), N($C_1$–$C_{12}$alkyl)$_2$, NH-phenyl or N($C_1$–$C_{12}$alkyl)-phenyl; and $R_8$ is H, OH, $C_1$–$C_{12}$alkyl, $C_1$–$C_{12}$alkoxy, $C_1$–$C_6$alkoxy-$C_1$–$C_6$alkoxy, $C_2$–$C_8$alkenyloxy, phenyl, phenoxy, benzyloxy, $NH_2$, NH($C_1$–$C_{12}$alkyl), N($C_1$–$C_{12}$alkyl)$_2$, NH-phenyl or N($C_1$–$C_{12}$alkyl)-phenyl;

or, where applicable, an E/Z isomer, a mixture of E/Z isomers and/or a tautomer, in each case in free form or in salt form.

2. A pesticidal composition comprising as an active ingredient at least one compound of formula (I) as claimed in claim 1, and at least one adjuvant.

3. A method of controlling pests, which comprises applying the composition as claimed in claim 2 to the pests or to the locus thereof.

4. A process for the preparation of a composition as claimed as in claim 2 comprising at least one adjuvant, which comprises intimately mixing and/or grinding the active ingredient with the adjuvant(s).

5. A method for the protection of plant propagation material, which comprises treating the propagation material or the planting site of the propagation material with the composition as claimed in claim 2.

6. Plant propagation material treated in accordance with the method described in claim 5.

* * * * *